US011466066B2

(12) United States Patent
Pancook et al.

(10) Patent No.: US 11,466,066 B2
(45) Date of Patent: Oct. 11, 2022

(54) VARIANTS OF HUMAN BMP7 PROTEIN

(71) Applicant: ELI LILLY AND COMPANY, Indianapolis, IN (US)

(72) Inventors: James David Pancook, Indianapolis, IN (US); Scott William Rowlinson, Indianapolis, IN (US); Louis Frank Stancato, Indianapolis, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 205 days.

(21) Appl. No.: 16/608,015

(22) PCT Filed: Apr. 20, 2018

(86) PCT No.: PCT/US2018/028496
§ 371 (c)(1),
(2) Date: Oct. 24, 2019

(87) PCT Pub. No.: WO2018/200322
PCT Pub. Date: Nov. 1, 2018

(65) Prior Publication Data
US 2021/0115100 A1   Apr. 22, 2021

Related U.S. Application Data

(60) Provisional application No. 62/490,910, filed on Apr. 27, 2017.

(51) Int. Cl.
| C07K 14/51 | (2006.01) |
| A61P 35/00 | (2006.01) |
| A61K 45/06 | (2006.01) |
| C07K 16/28 | (2006.01) |
| A61K 38/00 | (2006.01) |
| A61N 5/00 | (2006.01) |

(52) U.S. Cl.
CPC .............. *C07K 14/51* (2013.01); *A61K 45/06* (2013.01); *A61P 35/00* (2018.01); *C07K 16/2857* (2013.01); *A61K 38/00* (2013.01); *A61N 5/00* (2013.01)

(58) Field of Classification Search
None
See application file for complete search history.

(56) References Cited

U.S. PATENT DOCUMENTS

2009/0093427 A1   4/2009   Fisher

FOREIGN PATENT DOCUMENTS

| WO | WO-2005097825 A2 | 10/2005 |
| WO | WO-2008082563 A2 | 7/2008 |
| WO | WO-2008151258 A2 | 12/2008 |
| WO | WO-2009086131 A1 | 7/2009 |

OTHER PUBLICATIONS

Cortez et al. ("Bone morphogenetic protein 7 promotes resistance to immunotherapy" Nature Communications; (2020) 11:4840).*
Aoki et al. ("Expression of Bone Morphogenic Protein-7 significantly correlates with non-small cell lung cancer progression and prognosis: A retrospective cohort study", Clinical Medicine Insights: Oncology vol. 13; 1-6, 2019).*
Alarmo et al. ("BMP-7 influences proliferation, migration and invasion of breast cancer cells" Cancer Letters; vol. 275, Issue 1, 2009, p. 35-43).*
cancer.gov (accessed Dec. 20, 2021).*
International Search Report and Written Opinion for PCT Application No. PCT/US2018/028496 dated Jul. 27, 2018 (11 pages).
Tate et al. "A BMP7 variant inhibits the tumorigenic potential of glioblastoma stem-like cells" Cell Death and Differentiation (2012) 19, 1644-1654.
Veschi et al. "Targeting chemoresistant colorectal cancer via systemic administration of a BMP7 variant" Oncogene (2020) 39: 987-1003.
Tate et al. "A BMP7 Variant Inhibits Tumor Angiogenesis In Vitro and In Vivo through Direct Modulation of Endothelial Cell Biolo" PLOS ONE | DOI:10.1371/journal.pone.0125697 Apr. 28, 2015, 1-20.

* cited by examiner

*Primary Examiner* — Julie Ha
*Assistant Examiner* — Tara L Martinez
(74) *Attorney, Agent, or Firm* — Goodwin Procter LLP

(57) ABSTRACT

The present invention relates to novel variants of human BMP7 protein. The invention embodies vectors and host cells for the propagation of nucleic acid sequences encoding said proteins and the production thereof. Also disclosed are methods for the treatment of cancer, cartilage damage and degeneration, pain associated with osteoarthritis, or bone healing.

16 Claims, No Drawings
Specification includes a Sequence Listing.

SEQUENCE LISTING

<160> NUMBER OF SEQ ID NOS: 21

<210> SEQ ID NO 1
<211> LENGTH: 431
<212> TYPE: PRT
<213> ORGANISM: Homo sapiens

<400> SEQUENCE: 1

```
Met His Val Arg Ser Leu Arg Ala Ala Ala Pro His Ser Phe Val Ala
1               5                  10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255
```

-continued

Ile Asn Pro Lys Leu Ala Gly Leu Ile Gly Arg His Gly Pro Gln Asn
            260                 265                 270

Lys Gln Pro Phe Met Val Ala Phe Lys Ala Thr Glu Val His Phe
        275                 280                 285

Arg Ser Ile Arg Ser Thr Gly Ser Lys Gln Arg Ser Gln Asn Arg Ser
        290                 295                 300

Lys Thr Pro Lys Asn Gln Glu Ala Leu Arg Met Ala Asn Val Ala Glu
305                 310                 315                 320

Asn Ser Ser Asp Gln Arg Gln Ala Cys Lys Lys His Glu Leu Tyr
            325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
        370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
            405                 410                 415

Leu Lys Lys Tyr Arg Asn Met Val Val Arg Ala Cys Gly Cys His
            420                 425                 430

<210> SEQ ID NO 2
<211> LENGTH: 139
<212> TYPE: PRT
<213> ORGANISM: Homo sapiens

<400> SEQUENCE: 2

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
            85                  90                  95

Glu Thr Val Pro Lys Pro Cys Cys Ala Pro Thr Gln Leu Asn Ala Ile
        100                 105                 110

Ser Val Leu Tyr Phe Asp Asp Ser Ser Asn Val Ile Leu Lys Lys Tyr
    115                 120                 125

Arg Asn Met Val Val Arg Ala Cys Gly Cys His
        130                 135

<210> SEQ ID NO 3
<211> LENGTH: 139
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (33)..(33)

```
<223> OTHER INFORMATION: Xaa at position 33 = D or M
<220> FEATURE:
<221> NAME/KEY: MISC_FEATURE
<222> LOCATION: (37)..(37)
<223> OTHER INFORMATION: Xaa at position 37 = A or P
<220> FEATURE:
<221> NAME/KEY: MISC_FEATURE
<222> LOCATION: (60)..(60)
<223> OTHER INFORMATION: Xaa at position 60 = E or Q
<220> FEATURE:
<221> NAME/KEY: MISC_FEATURE
<222> LOCATION: (65)..(65)
<223> OTHER INFORMATION: Xaa at position 65 = Y, S, or G
<220> FEATURE:
<221> NAME/KEY: MISC_FEATURE
<222> LOCATION: (86)..(86)
<223> OTHER INFORMATION: Xaa at position 86 = I, V, or L
<220> FEATURE:
<221> NAME/KEY: MISC_FEATURE
<222> LOCATION: (87)..(87)
<223> OTHER INFORMATION: Xaa at position 87 = V or L
<220> FEATURE:
<221> NAME/KEY: MISC_FEATURE
<222> LOCATION: (89)..(89)
<223> OTHER INFORMATION: Xaa at position 89 = T, S, or A
<220> FEATURE:
<221> NAME/KEY: MISC_FEATURE
<222> LOCATION: (91)..(91)
<223> OTHER INFORMATION: Xaa at position 91 = V or M
<220> FEATURE:
<221> NAME/KEY: MISC_FEATURE
<222> LOCATION: (93)..(93)
<223> OTHER INFORMATION: Xaa at position 93 = F or V
<220> FEATURE:
<221> NAME/KEY: MISC_FEATURE
<222> LOCATION: (94)..(94)
<223> OTHER INFORMATION: Xaa at position 94 = I, F, or M
<220> FEATURE:
<221> NAME/KEY: MISC_FEATURE
<222> LOCATION: (110)..(110)
<223> OTHER INFORMATION: Xaa at position 110 = N, A, S, or G
<220> FEATURE:
<221> NAME/KEY: MISC_FEATURE
<222> LOCATION: (114)..(114)
<223> OTHER INFORMATION: Xaa at position 114 = V or M
<220> FEATURE:
<221> NAME/KEY: MISC_FEATURE
<222> LOCATION: (120)..(120)
<223> OTHER INFORMATION: Xaa at position 120 = S or Q
<220> FEATURE:
<221> NAME/KEY: MISC_FEATURE
<222> LOCATION: (128)..(128)
<223> OTHER INFORMATION: Xaa at position 128 = Y, F or W
<220> FEATURE:
<221> NAME/KEY: MISC_FEATURE
<222> LOCATION: (132)..(132)
<223> OTHER INFORMATION: Xaa at position 132 = V, Q, or S
<220> FEATURE:
<221> NAME/KEY: MISC_FEATURE
<222> LOCATION: (134)..(134)
<223> OTHER INFORMATION: Xaa at position 134 = R or K

<400> SEQUENCE: 3

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Xaa Gln Arg Gln Xaa Cys Lys Lys His Glu Leu Tyr Val Ser Phe Arg
        35                  40                  45

Asp Leu Gly Trp Gln Asp Trp Ile Ile Ala Pro Xaa Gly Tyr Ala Ala
    50                  55                  60

Xaa Tyr Cys Glu Gly Glu Cys Ala Phe Pro Leu Asn Ser Tyr Met Asn
65                  70                  75                  80
```

```
Ala Thr Asn His Ala Xaa Xaa Gln Xaa Leu Xaa His Xaa Xaa Asn Pro
                 85                  90                  95

Glu Thr Val Pro Lys Pro Cys Cys Ala Pro Thr Gln Leu Xaa Ala Ile
            100                 105                 110

Ser Xaa Leu Tyr Phe Asp Asp Xaa Ser Asn Val Ile Leu Lys Lys Xaa
        115                 120                 125

Arg Asn Met Xaa Val Xaa Ala Cys Gly Cys His
    130                 135
```

<210> SEQ ID NO 4
<211> LENGTH: 139
<212> TYPE: PRT
<213> ORGANISM: Artificial Sequence
<220> FEATURE:
<223> OTHER INFORMATION: Synthetic construct

<400> SEQUENCE: 4

```
Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Val Ile Asn Pro
                85                  90                  95

Glu Thr Val Pro Lys Pro Cys Cys Ala Pro Thr Gln Leu Gly Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135
```

<210> SEQ ID NO 5
<211> LENGTH: 139
<212> TYPE: PRT
<213> ORGANISM: Artificial Sequence
<220> FEATURE:
<223> OTHER INFORMATION: Synthetic construct

<400> SEQUENCE: 5

```
Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Gly Tyr Cys Glu Gly Gly Cys Ala Phe Pro Leu Asn Ser Tyr Met Asn
65                  70                  75                  80

Ala Thr Asn His Ala Leu Val Gln Ala Leu Val His Phe Ile Asn Pro
                85                  90                  95

Glu Thr Val Pro Lys Pro Cys Cys Ala Pro Thr Gln Leu Gly Ala Ile
            100                 105                 110
```

```
Ser Val Leu Tyr Phe Asp Asp Ser Ser Asn Val Ile Leu Lys Lys Tyr
        115                 120                 125

Arg Asn Met Val Val Arg Ala Cys Gly Cys His
        130                 135

<210> SEQ ID NO 6
<211> LENGTH: 139
<212> TYPE: PRT
<213> ORGANISM: Artificial Sequence
<220> FEATURE:
<223> OTHER INFORMATION: Synthetic construct

<400> SEQUENCE: 6

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Gly Tyr Cys Glu Gly Glu Cys Ala Phe Pro Leu Asn Ser Tyr Met Asn
65                  70                  75                  80

Ala Thr Asn His Ala Leu Val Gln Thr Leu Val His Phe Ile Asn Pro
                85                  90                  95

Glu Thr Val Pro Lys Pro Cys Cys Ala Pro Thr Gln Leu Gly Ala Ile
            100                 105                 110

Ser Val Leu Tyr Phe Asp Asp Ser Ser Asn Val Ile Leu Lys Lys Phe
        115                 120                 125

Arg Asn Met Val Val Arg Ala Cys Gly Cys His
        130                 135

<210> SEQ ID NO 7
<211> LENGTH: 139
<212> TYPE: PRT
<213> ORGANISM: Artificial Sequence
<220> FEATURE:
<223> OTHER INFORMATION: Synthetic construct

<400> SEQUENCE: 7

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Gly Tyr Cys Glu Gly Glu Cys Ala Phe Pro Leu Asn Ser Tyr Met Asn
65                  70                  75                  80

Ala Thr Asn His Ala Leu Val Gln Thr Leu Val His Phe Ile Asn Pro
                85                  90                  95

Glu Thr Val Pro Lys Pro Cys Cys Ala Pro Thr Gln Leu Gly Ala Ile
            100                 105                 110

Ser Val Leu Tyr Phe Asp Asp Ser Ser Asn Val Ile Leu Lys Lys Trp
        115                 120                 125

Arg Asn Met Val Val Arg Ala Cys Gly Cys His
```

<210> SEQ ID NO 8
<211> LENGTH: 139
<212> TYPE: PRT
<213> ORGANISM: Artificial Sequence
<220> FEATURE:
<223> OTHER INFORMATION: Synthetic construct

<400> SEQUENCE: 8

```
Ser Thr Gly Ser Lys Gln Arg Ser Gln Asn Arg Ser Lys Thr Pro Lys
 1               5                  10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Gly Tyr Cys Glu Gly Glu Cys Ala Phe Pro Leu Asn Ser Tyr Met Asn
65                  70                  75                  80

Ala Thr Asn His Ala Leu Val Gln Thr Leu Val His Val Ile Asn Pro
                85                  90                  95

Glu Thr Val Pro Lys Pro Cys Cys Ala Pro Thr Gln Leu Gly Ala Ile
            100                 105                 110

Ser Val Leu Tyr Phe Asp Asp Ser Ser Asn Val Ile Leu Lys Lys Trp
        115                 120                 125

Arg Asn Met Val Val Arg Ala Cys Gly Cys His
    130                 135
```

<210> SEQ ID NO 9
<211> LENGTH: 139
<212> TYPE: PRT
<213> ORGANISM: Artificial Sequence
<220> FEATURE:
<223> OTHER INFORMATION: Synthetic construct

<400> SEQUENCE: 9

```
Ser Thr Gly Ser Lys Gln Arg Ser Gln Asn Arg Ser Lys Thr Pro Lys
 1               5                  10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Gly Tyr Cys Glu Gly Glu Cys Ala Phe Pro Leu Asn Ser Tyr Met Asn
65                  70                  75                  80

Ala Thr Asn His Ala Ile Val Gln Ala Leu Val His Phe Ile Asn Pro
                85                  90                  95

Glu Thr Val Pro Lys Pro Cys Cys Ala Pro Thr Gln Leu Gly Ala Ile
            100                 105                 110

Ser Val Leu Tyr Phe Asp Asp Ser Ser Asn Val Ile Leu Lys Lys Phe
        115                 120                 125

Arg Asn Met Val Val Arg Ala Cys Gly Cys His
    130                 135
```

<210> SEQ ID NO 10
<211> LENGTH: 139

```
<212> TYPE: PRT
<213> ORGANISM: Artificial Sequence
<220> FEATURE:
<223> OTHER INFORMATION: Synthetic construct

<400> SEQUENCE: 10

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Gly Tyr Cys Glu Gly Glu Cys Ala Phe Pro Leu Asn Ser Tyr Met Asn
65                  70                  75                  80

Ala Thr Asn His Ala Leu Val Gln Thr Leu Val His Phe Ile Asn Pro
                85                  90                  95

Glu Thr Val Pro Lys Pro Cys Cys Ala Pro Thr Gln Leu Gly Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 11
<211> LENGTH: 139
<212> TYPE: PRT
<213> ORGANISM: Artificial Sequence
<220> FEATURE:
<223> OTHER INFORMATION: Synthetic construct

<400> SEQUENCE: 11

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Gly Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Met Leu Tyr Phe Asp Asp Ser Ser Asn Val Ile Leu Lys Lys Tyr
        115                 120                 125

Arg Asn Met Val Val Arg Ala Cys Gly Cys His
    130                 135

<210> SEQ ID NO 12
<211> LENGTH: 402
<212> TYPE: PRT
<213> ORGANISM: Artificial Sequence
<220> FEATURE:
<223> OTHER INFORMATION: Synthetic construct
```

<400> SEQUENCE: 12

```
Asp Phe Ser Leu Asp Asn Glu Val His Ser Phe Ile His Arg Arg
1               5                   10                  15

Leu Arg Ser Gln Glu Arg Arg Glu Met Gln Arg Glu Ile Leu Ser Ile
            20                  25                  30

Leu Gly Leu Pro His Arg Pro Arg Pro His Leu Gln Gly Lys His Asn
        35                  40                  45

Ser Ala Pro Met Phe Met Leu Asp Leu Tyr Asn Ala Met Ala Val Glu
    50                  55                  60

Glu Gly Gly Gly Pro Gly Gly Gln Gly Phe Ser Tyr Pro Tyr Lys Ala
65                  70                  75                  80

Val Phe Ser Thr Gln Gly Pro Pro Leu Ala Ser Leu Gln Asp Ser His
            85                  90                  95

Phe Leu Thr Asp Ala Asp Met Val Met Ser Phe Val Asn Leu Val Glu
        100                 105                 110

His Asp Lys Glu Phe Phe His Pro Arg Tyr His His Arg Glu Phe Arg
    115                 120                 125

Phe Asp Leu Ser Lys Ile Pro Glu Gly Glu Ala Val Thr Ala Ala Glu
130                 135                 140

Phe Arg Ile Tyr Lys Asp Tyr Ile Arg Glu Arg Phe Asp Asn Glu Thr
145                 150                 155                 160

Phe Arg Ile Ser Val Tyr Gln Val Leu Gln Glu His Leu Gly Arg Glu
            165                 170                 175

Ser Asp Leu Phe Leu Leu Asp Ser Arg Thr Leu Trp Ala Ser Glu Glu
        180                 185                 190

Gly Trp Leu Val Phe Asp Ile Thr Ala Thr Ser Asn His Trp Val Val
    195                 200                 205

Asn Pro Arg His Asn Leu Gly Leu Gln Leu Ser Val Glu Thr Leu Asp
210                 215                 220

Gly Gln Ser Ile Asn Pro Lys Leu Ala Gly Leu Ile Gly Arg His Gly
225                 230                 235                 240

Pro Gln Asn Lys Gln Pro Phe Met Val Ala Phe Phe Lys Ala Thr Glu
            245                 250                 255

Val His Phe Arg Ser Ile Arg Ser Thr Gly Ser Lys Gln Arg Ser Gln
        260                 265                 270

Asn Arg Ser Lys Thr Pro Lys Asn Gln Glu Ala Leu Arg Met Ala Asn
    275                 280                 285

Val Ala Glu Asn Ser Ser Asp Gln Arg Gln Ala Cys Lys Lys His
290                 295                 300

Glu Leu Tyr Val Ser Phe Arg Asp Leu Gly Trp Gln Asp Trp Ile Ile
305                 310                 315                 320

Ala Pro Glu Gly Tyr Ala Ala Tyr Tyr Cys Glu Gly Glu Cys Ala Phe
            325                 330                 335

Pro Leu Asn Ser Tyr Met Asn Ala Thr Asn His Ala Ile Val Gln Thr
        340                 345                 350

Leu Val His Val Ile Asn Pro Glu Thr Val Pro Lys Pro Cys Cys Ala
    355                 360                 365

Pro Thr Gln Leu Gly Ala Ile Ser Val Leu Tyr Phe Asp Asp Ser Ser
370                 375                 380

Asn Val Ile Leu Lys Lys Tyr Arg Asn Met Val Val Arg Ala Cys Gly
385                 390                 395                 400

Cys His
```

```
<210> SEQ ID NO 13
<211> LENGTH: 402
<212> TYPE: PRT
<213> ORGANISM: Artificial Sequence
<220> FEATURE:
<223> OTHER INFORMATION: Synthetic construct

<400> SEQUENCE: 13

Asp Phe Ser Leu Asp Asn Glu Val His Ser Phe Ile His Arg Arg
1               5                   10                  15

Leu Arg Ser Gln Glu Arg Arg Glu Met Gln Arg Glu Ile Leu Ser Ile
            20                  25                  30

Leu Gly Leu Pro His Arg Pro Arg Pro His Leu Gln Gly Lys His Asn
        35                  40                  45

Ser Ala Pro Met Phe Met Leu Asp Leu Tyr Asn Ala Met Ala Val Glu
    50                  55                  60

Glu Gly Gly Gly Pro Gly Gly Gln Gly Phe Ser Tyr Pro Tyr Lys Ala
65                  70                  75                  80

Val Phe Ser Thr Gln Gly Pro Pro Leu Ala Ser Leu Gln Asp Ser His
                85                  90                  95

Phe Leu Thr Asp Ala Asp Met Val Met Ser Phe Val Asn Leu Val Glu
            100                 105                 110

His Asp Lys Glu Phe Phe His Pro Arg Tyr His His Arg Glu Phe Arg
        115                 120                 125

Phe Asp Leu Ser Lys Ile Pro Glu Gly Glu Ala Val Thr Ala Ala Glu
    130                 135                 140

Phe Arg Ile Tyr Lys Asp Tyr Ile Arg Glu Arg Phe Asp Asn Glu Thr
145                 150                 155                 160

Phe Arg Ile Ser Val Tyr Gln Val Leu Gln Glu His Leu Gly Arg Glu
                165                 170                 175

Ser Asp Leu Phe Leu Leu Asp Ser Arg Thr Leu Trp Ala Ser Glu Glu
            180                 185                 190

Gly Trp Leu Val Phe Asp Ile Thr Ala Thr Ser Asn His Trp Val Val
        195                 200                 205

Asn Pro Arg His Asn Leu Gly Leu Gln Leu Ser Val Glu Thr Leu Asp
    210                 215                 220

Gly Gln Ser Ile Asn Pro Lys Leu Ala Gly Leu Ile Gly Arg His Gly
225                 230                 235                 240

Pro Gln Asn Lys Gln Pro Phe Met Val Ala Phe Phe Lys Ala Thr Glu
                245                 250                 255

Val His Phe Arg Ser Ile Arg Ser Thr Gly Ser Lys Gln Arg Ser Gln
            260                 265                 270

Asn Arg Ser Lys Thr Pro Lys Asn Gln Glu Ala Leu Arg Met Ala Asn
        275                 280                 285

Val Ala Glu Asn Ser Ser Asp Gln Arg Gln Ala Cys Lys Lys His
    290                 295                 300

Glu Leu Tyr Val Ser Phe Arg Asp Leu Gly Trp Gln Asp Trp Ile Ile
305                 310                 315                 320

Ala Pro Glu Gly Tyr Ala Ala Gly Tyr Cys Glu Gly Glu Cys Ala Phe
                325                 330                 335

Pro Leu Asn Ser Tyr Met Asn Ala Thr Asn His Ala Leu Val Gln Ala
            340                 345                 350

Leu Val His Phe Ile Asn Pro Glu Thr Val Pro Lys Pro Cys Cys Ala
        355                 360                 365
```

```
Pro Thr Gln Leu Gly Ala Ile Ser Val Leu Tyr Phe Asp Asp Ser Ser
    370                 375                 380

Asn Val Ile Leu Lys Lys Tyr Arg Asn Met Val Val Arg Ala Cys Gly
385                 390                 395                 400

Cys His

<210> SEQ ID NO 14
<211> LENGTH: 402
<212> TYPE: PRT
<213> ORGANISM: Artificial Sequence
<220> FEATURE:
<223> OTHER INFORMATION: Synthetic construct

<400> SEQUENCE: 14

Asp Phe Ser Leu Asp Asn Glu Val His Ser Phe Ile His Arg Arg
1               5                   10                  15

Leu Arg Ser Gln Glu Arg Glu Met Gln Arg Glu Ile Leu Ser Ile
                20                  25                  30

Leu Gly Leu Pro His Arg Pro Arg Pro His Leu Gln Gly Lys His Asn
                35                  40                  45

Ser Ala Pro Met Phe Met Leu Asp Leu Tyr Asn Ala Met Ala Val Glu
50                  55                  60

Glu Gly Gly Gly Pro Gly Gly Gln Gly Phe Ser Tyr Pro Tyr Lys Ala
65                  70                  75                  80

Val Phe Ser Thr Gln Gly Pro Pro Leu Ala Ser Leu Gln Asp Ser His
                85                  90                  95

Phe Leu Thr Asp Ala Asp Met Val Met Ser Phe Val Asn Leu Val Glu
                100                 105                 110

His Asp Lys Glu Phe Phe His Pro Arg Tyr His His Arg Glu Phe Arg
            115                 120                 125

Phe Asp Leu Ser Lys Ile Pro Glu Gly Glu Ala Val Thr Ala Ala Glu
        130                 135                 140

Phe Arg Ile Tyr Lys Asp Tyr Ile Arg Glu Arg Phe Asp Asn Glu Thr
145                 150                 155                 160

Phe Arg Ile Ser Val Tyr Gln Val Leu Gln Glu His Leu Gly Arg Glu
                165                 170                 175

Ser Asp Leu Phe Leu Leu Asp Ser Arg Thr Leu Trp Ala Ser Glu Glu
            180                 185                 190

Gly Trp Leu Val Phe Asp Ile Thr Ala Thr Ser Asn His Trp Val Val
        195                 200                 205

Asn Pro Arg His Asn Leu Gly Leu Gln Leu Ser Val Glu Thr Leu Asp
210                 215                 220

Gly Gln Ser Ile Asn Pro Lys Leu Ala Gly Leu Ile Gly Arg His Gly
225                 230                 235                 240

Pro Gln Asn Lys Gln Pro Phe Met Val Ala Phe Phe Lys Ala Thr Glu
                245                 250                 255

Val His Phe Arg Ser Ile Arg Ser Thr Gly Ser Lys Gln Arg Ser Gln
            260                 265                 270

Asn Arg Ser Lys Thr Pro Lys Asn Gln Glu Ala Leu Arg Met Ala Asn
        275                 280                 285

Val Ala Glu Asn Ser Ser Ser Asp Gln Arg Gln Ala Cys Lys Lys His
290                 295                 300

Glu Leu Tyr Val Ser Phe Arg Asp Leu Gly Trp Gln Asp Trp Ile Ile
305                 310                 315                 320

Ala Pro Glu Gly Tyr Ala Ala Gly Tyr Cys Glu Gly Glu Cys Ala Phe
```

```
                    325                 330                 335
Pro Leu Asn Ser Tyr Met Asn Ala Thr Asn His Ala Leu Val Gln Thr
                340                 345                 350

Leu Val His Phe Ile Asn Pro Glu Thr Val Pro Lys Pro Cys Cys Ala
            355                 360                 365

Pro Thr Gln Leu Gly Ala Ile Ser Val Leu Tyr Phe Asp Asp Ser Ser
    370                 375                 380

Asn Val Ile Leu Lys Lys Phe Arg Asn Met Val Val Arg Ala Cys Gly
385                 390                 395                 400

Cys His

<210> SEQ ID NO 15
<211> LENGTH: 402
<212> TYPE: PRT
<213> ORGANISM: Artificial Sequence
<220> FEATURE:
<223> OTHER INFORMATION: Synthetic construct

<400> SEQUENCE: 15

Asp Phe Ser Leu Asp Asn Glu Val His Ser Phe Ile His Arg Arg
1               5                   10                  15

Leu Arg Ser Gln Glu Arg Arg Glu Met Gln Arg Glu Ile Leu Ser Ile
                20                  25                  30

Leu Gly Leu Pro His Arg Pro Arg Pro His Leu Gln Gly Lys His Asn
            35                  40                  45

Ser Ala Pro Met Phe Met Leu Asp Leu Tyr Asn Ala Met Ala Val Glu
    50                  55                  60

Glu Gly Gly Gly Pro Gly Gly Gln Gly Phe Ser Tyr Pro Tyr Lys Ala
65                  70                  75                  80

Val Phe Ser Thr Gln Gly Pro Pro Leu Ala Ser Leu Gln Asp Ser His
                85                  90                  95

Phe Leu Thr Asp Ala Asp Met Val Met Ser Phe Val Asn Leu Val Glu
            100                 105                 110

His Asp Lys Glu Phe Phe His Pro Arg Tyr His His Arg Glu Phe Arg
        115                 120                 125

Phe Asp Leu Ser Lys Ile Pro Glu Gly Glu Ala Val Thr Ala Ala Glu
    130                 135                 140

Phe Arg Ile Tyr Lys Asp Tyr Ile Arg Glu Arg Phe Asp Asn Glu Thr
145                 150                 155                 160

Phe Arg Ile Ser Val Tyr Gln Val Leu Gln Glu His Leu Gly Arg Glu
                165                 170                 175

Ser Asp Leu Phe Leu Leu Asp Ser Arg Thr Leu Trp Ala Ser Glu Glu
            180                 185                 190

Gly Trp Leu Val Phe Asp Ile Thr Ala Thr Ser Asn His Trp Val Val
        195                 200                 205

Asn Pro Arg His Asn Leu Gly Leu Gln Leu Ser Val Glu Thr Leu Asp
    210                 215                 220

Gly Gln Ser Ile Asn Pro Lys Leu Ala Gly Leu Ile Gly Arg His Gly
225                 230                 235                 240

Pro Gln Asn Lys Gln Pro Phe Met Val Ala Phe Phe Lys Ala Thr Glu
                245                 250                 255

Val His Phe Arg Ser Ile Arg Ser Thr Gly Ser Lys Gln Arg Ser Gln
            260                 265                 270

Asn Arg Ser Lys Thr Pro Lys Asn Gln Glu Ala Leu Arg Met Ala Asn
        275                 280                 285
```

Val Ala Glu Asn Ser Ser Asp Gln Arg Gln Ala Cys Lys Lys His
    290                 295                 300

Glu Leu Tyr Val Ser Phe Arg Asp Leu Gly Trp Gln Asp Trp Ile Ile
305                 310                 315                 320

Ala Pro Glu Gly Tyr Ala Ala Gly Tyr Cys Glu Gly Glu Cys Ala Phe
                325                 330                 335

Pro Leu Asn Ser Tyr Met Asn Ala Thr Asn His Ala Leu Val Gln Thr
            340                 345                 350

Leu Val His Phe Ile Asn Pro Glu Thr Val Pro Lys Pro Cys Cys Ala
        355                 360                 365

Pro Thr Gln Leu Gly Ala Ile Ser Val Leu Tyr Phe Asp Asp Ser Ser
370                 375                 380

Asn Val Ile Leu Lys Lys Trp Arg Asn Met Val Val Arg Ala Cys Gly
385                 390                 395                 400

Cys His

<210> SEQ ID NO 16
<211> LENGTH: 402
<212> TYPE: PRT
<213> ORGANISM: Artificial Sequence
<220> FEATURE:
<223> OTHER INFORMATION: Synthetic construct

<400> SEQUENCE: 16

Asp Phe Ser Leu Asp Asn Glu Val His Ser Ser Phe Ile His Arg Arg
1               5                   10                  15

Leu Arg Ser Gln Glu Arg Arg Glu Met Gln Arg Glu Ile Leu Ser Ile
            20                  25                  30

Leu Gly Leu Pro His Arg Pro Arg Pro His Leu Gln Gly Lys His Asn
        35                  40                  45

Ser Ala Pro Met Phe Met Leu Asp Leu Tyr Asn Ala Met Ala Val Glu
    50                  55                  60

Glu Gly Gly Gly Pro Gly Gly Gln Gly Phe Ser Tyr Pro Tyr Lys Ala
65                  70                  75                  80

Val Phe Ser Thr Gln Gly Pro Pro Leu Ala Ser Leu Gln Asp Ser His
                85                  90                  95

Phe Leu Thr Asp Ala Asp Met Val Met Ser Phe Val Asn Leu Val Glu
            100                 105                 110

His Asp Lys Glu Phe Phe His Pro Arg Tyr His His Arg Glu Phe Arg
        115                 120                 125

Phe Asp Leu Ser Lys Ile Pro Glu Gly Glu Ala Val Thr Ala Ala Glu
    130                 135                 140

Phe Arg Ile Tyr Lys Asp Tyr Ile Arg Glu Arg Phe Asp Asn Glu Thr
145                 150                 155                 160

Phe Arg Ile Ser Val Tyr Gln Val Leu Gln Glu His Leu Gly Arg Glu
                165                 170                 175

Ser Asp Leu Phe Leu Leu Asp Ser Arg Thr Leu Trp Ala Ser Glu Glu
            180                 185                 190

Gly Trp Leu Val Phe Asp Ile Thr Ala Thr Ser Asn His Trp Val Val
        195                 200                 205

Asn Pro Arg His Asn Leu Gly Leu Gln Leu Ser Val Glu Thr Leu Asp
    210                 215                 220

Gly Gln Ser Ile Asn Pro Lys Leu Ala Gly Leu Ile Gly Arg His Gly
225                 230                 235                 240

-continued

```
Pro Gln Asn Lys Gln Pro Phe Met Val Ala Phe Phe Lys Ala Thr Glu
                245                 250                 255

Val His Phe Arg Ser Ile Arg Ser Thr Gly Ser Lys Gln Arg Ser Gln
            260                 265                 270

Asn Arg Ser Lys Thr Pro Lys Asn Gln Glu Ala Leu Arg Met Ala Asn
        275                 280                 285

Val Ala Glu Asn Ser Ser Asp Gln Arg Gln Ala Cys Lys Lys His
    290                 295                 300

Glu Leu Tyr Val Ser Phe Arg Asp Leu Gly Trp Gln Asp Trp Ile Ile
305                 310                 315                 320

Ala Pro Glu Gly Tyr Ala Ala Gly Tyr Cys Glu Gly Glu Cys Ala Phe
                325                 330                 335

Pro Leu Asn Ser Tyr Met Asn Ala Thr Asn His Ala Leu Val Gln Thr
            340                 345                 350

Leu Val His Val Ile Asn Pro Glu Thr Val Pro Lys Pro Cys Cys Ala
        355                 360                 365

Pro Thr Gln Leu Gly Ala Ile Ser Val Leu Tyr Phe Asp Asp Ser Ser
    370                 375                 380

Asn Val Ile Leu Lys Lys Trp Arg Asn Met Val Val Arg Ala Cys Gly
385                 390                 395                 400

Cys His

<210> SEQ ID NO 17
<211> LENGTH: 139
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (33)..(33)
<223> OTHER INFORMATION: Xaa at position 33 = D or M
<220> FEATURE:
<221> NAME/KEY: MISC_FEATURE
<222> LOCATION: (37)..(37)
<223> OTHER INFORMATION: Xaa at position 37 = A or P
<220> FEATURE:
<221> NAME/KEY: MISC_FEATURE
<222> LOCATION: (60)..(60)
<223> OTHER INFORMATION: Xaa at position 60 = E or Q
<220> FEATURE:
<221> NAME/KEY: MISC_FEATURE
<222> LOCATION: (65)..(65)
<223> OTHER INFORMATION: Xaa at position 65 = Y, S, or G
<220> FEATURE:
<221> NAME/KEY: MISC_FEATURE
<222> LOCATION: (86)..(86)
<223> OTHER INFORMATION: Xaa at position 86 = I, V or L
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: MISC_FEATURE
<222> LOCATION: (91)..(91)
<223> OTHER INFORMATION: Xaa at position 91 = V or M
<220> FEATURE:
<221> NAME/KEY: MISC_FEATURE
<222> LOCATION: (93)..(93)
<223> OTHER INFORMATION: Xaa at 93 = F or V
<220> FEATURE:
<221> NAME/KEY: MISC_FEATURE
<222> LOCATION: (94)..(94)
<223> OTHER INFORMATION: Xaa at 94 = I, F or M
<220> FEATURE:
<221> NAME/KEY: MISC_FEATURE
<222> LOCATION: (110)..(110)
<223> OTHER INFORMATION: Xaa at position 110 = N, A, S or G
```

```
<220> FEATURE:
<221> NAME/KEY: MISC_FEATURE
<222> LOCATION: (114)..(114)
<223> OTHER INFORMATION: Xaa at position 114 = V or M
<220> FEATURE:
<221> NAME/KEY: MISC_FEATURE
<222> LOCATION: (128)..(128)
<223> OTHER INFORMATION: Xaa at position 128 = Y, F or W

<400> SEQUENCE: 17

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Xaa Gln Arg Gln Xaa Cys Lys Lys His Glu Leu Tyr Val Ser Phe Arg
        35                  40                  45

Asp Leu Gly Trp Gln Asp Trp Ile Ile Ala Pro Xaa Gly Tyr Ala Ala
    50                  55                  60

Xaa Tyr Cys Glu Gly Glu Cys Ala Phe Pro Leu Asn Ser Tyr Met Asn
65                  70                  75                  80

Ala Thr Asn His Ala Xaa Val Gln Xaa Leu Xaa His Xaa Xaa Asn Pro
                85                  90                  95

Glu Thr Val Pro Lys Pro Cys Cys Ala Pro Thr Gln Leu Xaa Ala Ile
            100                 105                 110

Ser Xaa Leu Tyr Phe Asp Asp Ser Ser Asn Val Ile Leu Lys Lys Xaa
        115                 120                 125

Arg Asn Met Val Val Arg Ala Cys Gly Cys His
    130                 135

<210> SEQ ID NO 18
<211> LENGTH: 257
<212> TYPE: PRT
<213> ORGANISM: Artificial Sequence
<220> FEATURE:
<223> OTHER INFORMATION: Synthetic construct

<400> SEQUENCE: 18

Asp Phe Ser Leu Asp Asn Glu Val His Ser Ser Phe Ile His Arg Arg
1               5                   10                  15

Leu Arg Ser Gln Glu Arg Arg Glu Met Gln Arg Glu Ile Leu Ser Ile
            20                  25                  30

Leu Gly Leu Pro His Arg Pro Arg Pro His Leu Gln Gly Lys His Asn
        35                  40                  45

Ser Ala Pro Met Phe Met Leu Asp Leu Tyr Asn Ala Met Ala Val Glu
    50                  55                  60

Glu Gly Gly Gly Pro Gly Gly Gln Gly Phe Ser Tyr Pro Tyr Lys Ala
65                  70                  75                  80

Val Phe Ser Thr Gln Gly Pro Pro Leu Ala Ser Leu Gln Asp Ser His
            85                  90                  95

Phe Leu Thr Asp Ala Asp Met Val Met Ser Phe Val Asn Leu Val Glu
            100                 105                 110

His Asp Lys Glu Phe Phe His Pro Arg Tyr His His Arg Glu Phe Arg
        115                 120                 125

Phe Asp Leu Ser Lys Ile Pro Glu Gly Glu Ala Val Thr Ala Ala Glu
    130                 135                 140

Phe Arg Ile Tyr Lys Asp Tyr Ile Arg Glu Arg Phe Asp Asn Glu Thr
145                 150                 155                 160

Phe Arg Ile Ser Val Tyr Gln Val Leu Gln Ser Asp Leu Phe Leu Leu
```

165                 170                 175
Asp Ser Arg Thr Leu Trp Ala Ser Glu Glu Gly Trp Leu Val Phe Asp
                180                 185                 190

Ile Thr Ala Thr Ser Asn His Trp Val Val Asn Pro Arg His Asn Leu
            195                 200                 205

Gly Leu Gln Leu Ser Val Glu Thr Leu Asp Gly Gln Ser Ile Asn Pro
        210                 215                 220

Lys Leu Ala Gly Leu Ile Gly Arg His Gly Pro Gln Asn Lys Gln Pro
225                 230                 235                 240

Phe Met Val Ala Phe Phe Lys Ala Thr Glu Val His Phe Arg Ser Ile
                245                 250                 255

Arg

<210> SEQ ID NO 19
<211> LENGTH: 1293
<212> TYPE: DNA
<213> ORGANISM: Artificial Sequence
<220> FEATURE:
<223> OTHER INFORMATION: Synthetic construct

<400> SEQUENCE: 19
atgcacgtgc gcagcctgcg cgccgccgcc ccccacagct tcgtggccct gtgggccccc      60
ctgttcctgc tgcgcagcgc cctggccgac ttcagcctgg acaacgaggt gcacagcagc     120
ttcatccacc gccgcctgcg cagccaggag cgccgcgaga tgcagcgcga gatcctgagc     180
atcctgggcc tgccccaccg ccccgcccc cacctgcagg gcaagcacaa cagcgccccc      240
atgttcatgc tggacctgta caacgccatg gccgtggagg agggcggcgg ccccggcggc     300
cagggcttca gctaccccta caaggccgtg ttcagcaccc agggcccccc cctggccagc     360
ctgcaggaca gccacttcct gaccgacgcc gacatggtga tgagcttcgt gaacctggtg     420
gagcacgaca aggagttctt ccaccccgc taccaccacc gcgagttccg cttcgacctg      480
agcaagatcc ccgagggcga ggccgtgacc gccgccgagt ccgcatcta caaggactac     540
atccgcgagc gcttcgacaa cgagaccttc cgcatcagcg tgtaccaggt gctgcaggag     600
cacctgggcc gcgagagcga cctgttcctg ctggacagcg caccctgtg gccagcgag      660
gagggctggc tggtgttcga catcaccgcc accagcaacc actgggtggt gaaccccgc      720
cacaacctgg gcctgcagct gagcgtggag accctggacg gccagagcat caaccccaag    780
ctggccggcc tgatcggccg ccacggcccc cagaacaagc agcccttcat ggtggccttc    840
ttcaaggcca ccgaggtgca cttccgcagc atccgcagca ccggcagcaa gcagcgcagc    900
cagaaccgca gcaagacccc caagaaccag gaggccctgc gcatggccaa cgtggccgag    960
aacagcagca cgaccagcg ccaggcctgc aagaagcacg agctgtacgt gagcttccgc     1020
gacctgggct ggcaggactg gatcatcgcc cctgagggct acgccgccgg ctactgcgag    1080
ggcgagtgcg ccttccccct gaacagctac atgaacgcca ccaaccacgc cctggtgcag    1140
accctggtgc acttcatcaa ccccgagacc gtgcccaagc cctgctgcgc ccccacccag    1200
ctgggcgcca tcagcgtgct gtacttcgac gacagcagca cgtgatcct gaagaagtgg    1260
cgcaacatgg tggtgcgcgc ctgcggctgc cac                                 1293

<210> SEQ ID NO 20
<211> LENGTH: 1293
<212> TYPE: DNA
<213> ORGANISM: Artificial Sequence
<220> FEATURE:

<223> OTHER INFORMATION: Synthetic construct

<400> SEQUENCE: 20

```
atgcacgtgc gcagcctgcg cgccgccgcc ccccacagct tcgtggccct gtgggccccc        60
ctgttcctgc tgcgcagcgc cctggccgac ttcagcctgg acaacgaggt gcacagcagc       120
ttcatccacc gccgcctgcg cagccaggag cgccgcgaga tgcagcgcga gatcctgagc       180
atcctgggcc tgccccaccg ccccgcccc acctgcagg gcaagcacaa cagcgccccc         240
atgttcatgc tggacctgta caacgccatg gccgtggagg agggcggcgg ccccggcggc       300
cagggcttca gctacccta caaggccgtg ttcagcaccc agggcccccc cctggccagc        360
ctgcaggaca gccacttcct gaccgacgcc gacatggtga tgagcttcgt gaacctggtg       420
gagcacgaca aggagttctt ccaccccgc taccaccacc gcgagttccg cttcgacctg        480
agcaagatcc ccgagggcga ggccgtgacc gccgccgagt ccgcatcta caaggactac        540
atccgcgagc gcttcgacaa cgagaccttc gcatcagcg tgtaccaggt gctgcaggag        600
cacctgggcc gcgagagcga cctgttcctg ctggacagcc gcaccctgtg gccagcgag        660
gagggctggc tggtgttcga catcaccgcc accagcaacc actgggtggt gaaccccgc        720
cacaacctgg gcctgcagct gagcgtggag accctggacg ccagagcat caaccccaag       780
ctggccggcc tgatcggccg ccacggcccc cagaacaagc agcccttcat ggtggccttc       840
ttcaaggcca ccgaggtgca cttccgcagc atccgcagca ccggcagcaa gcagcgcagc      900
cagaaccgca gcaagacccc caagaaccag gaggccctgc gcatggccaa cgtggccgag       960
aacagcagca gcgaccagcg ccaggcctgc aagaagcacg agctgtacgt gagcttccgc       1020
gacctgggct ggcaggactg gatcatcgcc cctgagggct acgccgccgg ctactgcgag      1080
ggcgagtgcg ccttccccct gaacagctac atgaacgcca ccaaccacgc cctggtgcag       1140
accctggtgc acgtgatcaa ccccgagacc gtgcccaagc cctgctgcgc ccccacccag       1200
ctgggcgcca tcagcgtgct gtacttcgac gacagcagca acgtgatcct gaagaagtgg      1260
cgcaacatgg tggtgcgcgc ctgcggctgc cac                                    1293
```

<210> SEQ ID NO 21
<211> LENGTH: 402
<212> TYPE: PRT
<213> ORGANISM: Homo sapiens

<400> SEQUENCE: 21

```
Asp Phe Ser Leu Asp Asn Glu Val His Ser Ser Phe Ile His Arg Arg
1               5                   10                  15

Leu Arg Ser Gln Glu Arg Arg Glu Met Gln Arg Glu Ile Leu Ser Ile
            20                  25                  30

Leu Gly Leu Pro His Arg Pro Arg Pro His Leu Gln Gly Lys His Asn
        35                  40                  45

Ser Ala Pro Met Phe Met Leu Asp Leu Tyr Asn Ala Met Ala Val Glu
    50                  55                  60

Glu Gly Gly Gly Pro Gly Gly Gln Gly Phe Ser Tyr Pro Tyr Lys Ala
65                  70                  75                  80

Val Phe Ser Thr Gln Gly Pro Pro Leu Ala Ser Leu Gln Asp Ser His
                85                  90                  95

Phe Leu Thr Asp Ala Asp Met Val Met Ser Phe Val Asn Leu Val Glu
            100                 105                 110

His Asp Lys Glu Phe Phe His Pro Arg Tyr His His Arg Glu Phe Arg
        115                 120                 125
```

```
Phe Asp Leu Ser Lys Ile Pro Glu Gly Glu Ala Val Thr Ala Ala Glu
        130                 135                 140

Phe Arg Ile Tyr Lys Asp Tyr Ile Arg Glu Arg Phe Asp Asn Glu Thr
145                 150                 155                 160

Phe Arg Ile Ser Val Tyr Gln Val Leu Gln Glu His Leu Gly Arg Glu
                165                 170                 175

Ser Asp Leu Phe Leu Leu Asp Ser Arg Thr Leu Trp Ala Ser Glu Glu
            180                 185                 190

Gly Trp Leu Val Phe Asp Ile Thr Ala Thr Ser Asn His Trp Val Val
        195                 200                 205

Asn Pro Arg His Asn Leu Gly Leu Gln Leu Ser Val Glu Thr Leu Asp
        210                 215                 220

Gly Gln Ser Ile Asn Pro Lys Leu Ala Gly Leu Ile Gly Arg His Gly
225                 230                 235                 240

Pro Gln Asn Lys Gln Pro Phe Met Val Ala Phe Phe Lys Ala Thr Glu
                245                 250                 255

Val His Phe Arg Ser Ile Arg Ser Thr Gly Ser Lys Gln Arg Ser Gln
                260                 265                 270

Asn Arg Ser Lys Thr Pro Lys Asn Gln Glu Ala Leu Arg Met Ala Asn
        275                 280                 285

Val Ala Glu Asn Ser Ser Ser Asp Gln Arg Gln Ala Cys Lys Lys His
        290                 295                 300

Glu Leu Tyr Val Ser Phe Arg Asp Leu Gly Trp Gln Asp Trp Ile Ile
305                 310                 315                 320

Ala Pro Glu Gly Tyr Ala Ala Tyr Tyr Cys Glu Gly Glu Cys Ala Phe
                325                 330                 335

Pro Leu Asn Ser Tyr Met Asn Ala Thr Asn His Ala Ile Val Gln Thr
            340                 345                 350

Leu Val His Phe Ile Asn Pro Glu Thr Val Pro Lys Pro Cys Cys Ala
        355                 360                 365

Pro Thr Gln Leu Asn Ala Ile Ser Val Leu Tyr Phe Asp Asp Ser Ser
370                 375                 380

Asn Val Ile Leu Lys Lys Tyr Arg Asn Met Val Val Arg Ala Cys Gly
385                 390                 395                 400

Cys His
```

VARIANTS OF HUMAN BMP7 PROTEIN

CROSS-REFERENCE TO RELATED APPLICATIONS

This application is a U.S. national stage application under 35 U.S.C. § 371 of International Application No. PCT/US2018/028496, filed Apr. 20, 2018, which claims priority to and the benefit of U.S. Provisional Patent Application No. 62/490,910, filed on Apr. 27, 2017, each of which are incorporated herein by reference in their entirety.

SEQUENCE LISTING

The instant application contains a Sequence Listing which has been submitted via EFS-Web and is hereby incorporated by reference in its entirety. Said ASCII copy, created on Oct. 22, 2019, is named X21419WOSequenceListingST25.txt, and is 47,810 bytes in size.

The present invention is in the field of medicine, particularly in the field of therapeutic proteins. Specifically, the present invention relates to variants of human bone morphogenic protein-7 (BMP7) useful for the treatment of cancer, cartilage damage and degeneration, pain associated with osteoarthritis or bone healing.

Bone morphogenic proteins are a well-known family of growth factors that regulate cell proliferation, migration, differentiation and apoptosis in a number of tissues and organs. Human BMP7 is a secreted signaling molecule of the TGF-beta superfamily and was originally identified for its ability to induce bone formation. It is now recognized as a multifunctional cytokine which mediates growth and differentiation of many different cell types.

BMP7 has been used to promote bone formation, bone fracture healing and spinal fusion. Nevertheless, its use as a therapeutic has been limited primarily to topical administration to the surface of the tissue because of its poor solubility/bioavailability and the propensity to cause ectopic bone formation (EBF) or a rapid formation of new bone in soft tissue as a result of precipitation at the injection site.

BMP7 protein variants with improved properties such as increased expression yield, increased solubility, increased specific activity and decreased immunogenicity have been reported in WO2005/097825. However, there is still a need for human BMP7 protein variants with improved solubility/bioavailability, increased specific activity, decreased binding to endogenous circulating inhibitors, and reduced EBF activity that could be useful as a therapeutic.

Cancer stem-like cells (CSC) in solid tumors are purported to contribute to cancer development and poor treatment outcome. The abilities to self-renew, differentiate, and resist anticancer therapies are hallmarks of these rare cells, and steering them into lineage commitment may be one strategy to curb cancer development or progression. However, despite the acknowledged potential of this approach, there still remains a need for effective cancer therapies which induce tumor cell transdifferentiation and revert CSCs into lineages that are not resistant or less resistant to killing by conventional chemo- and radiotherapy (see, for example, Li, R., et al., Oncotarget. 2016 Oct. 18; 7(42): 68360-68370).

The present invention provides alternative human BMP7 protein variants. Particularly, the present invention provides variants of human BMP7 protein with increased specific activity, improved solubility/bioavailability characteristics, decreased binding to endogenous circulating inhibitors, and/or reduced EBF activity as compared to the corresponding wild type human BMP7 protein. In addition, a method of treating cancer, cartilage damage and degeneration, pain associated with osteoarthritis or bone fracture healing comprising the administration of a human BMP7 protein variant of the present invention is described.

The present invention provides a variant of human BMP7 protein wherein the mature domain of the human BMP7 protein comprises a polypeptide comprising the amino acid sequence of:

(SEQ ID NO: 3)
STGSKQRSQNRSKTPKNQEALRMANVAENSSSXaa$_{33}$QRQXaa$_{37}$CKK

HELYVSFRDLGWQDWIIAPXaa$_{60}$GYAAXaa$_{65}$YCEGECAFPLNSYMN

ATNHAXaa$_{86}$Xaa$_{87}$QXaa$_{89}$LXaa$_{91}$HXaa$_{93}$Xaa$_{94}$NPETVPKPCCAPT

QLXaa$_{110}$AISXaa$_{114}$LYFDDXaa$_{120}$SNVILKKXaa$_{128}$RNMXaa$_{132}$V

Xaa$_{134}$ACGCH, wherein

Xaa$_{33}$ is D or M; Xaa$_{37}$ is A or P; Xaa$_{60}$ is E or Q; Xaa$_{65}$ is Y, S, or G; Xaa$_{86}$ is I, V, or L; Xaa$_{87}$ is V or L; Xaa$_{89}$ is T, S, or A; Xaa$_{91}$ is V or M; Xaa$_{93}$ is F or V; Xaa$_{94}$ is I, F or M; Xaa$_{110}$ is G; Xaa$_{114}$ is V or M; Xaa$_{120}$ is S or Q; Xaa$_{128}$ is Y, F or W; Xaa$_{132}$ is V, Q, or S; and, Xaa$_{134}$ is R or K.

The invention also provides a variant of human BMP7 wherein the mature domain of the human BMP7 protein comprises a polypeptide comprising the amino acid sequence of SEQ ID NO: 3 wherein: (a) Xaa$_{33}$ is D; (b) Xaa$_{37}$ is A; (c) Xaa$_{60}$ is E; (d) Xaa$_{65}$ is Y, S, or G; (e) Xaa$_{86}$ is I, V, or L; (f) Xaa$_{87}$ is V; (g) Xaa$_{89}$ is T or A; (h) Xaa$_{91}$ is V; (i) Xaa$_{93}$ is F or V; (j) Xaa$_{94}$ is I; (k) Xaa$_{110}$ is G; (l) Xaa$_{114}$ is V or M; (m) Xaa$_{120}$ is S; (n) Xaa$_{128}$ is Y, F, or W; (o) Xaa$_{132}$ is V; and (p) Xaa$_{134}$ is R.

The invention also provides a variant of human BMP7 protein wherein the mature domain of the BMP7 protein comprises a polypeptide comprising the amino acid sequence of SEQ ID NO: 3 wherein: (a) Xaa$_{33}$ is D; (b) Xaa$_{37}$ is A; (c) Xaa$_{60}$ is E; (d) Xaa$_{65}$ is Y or G; (e) Xaa$_{86}$ is I or L; (f) Xaa$_{87}$ is V; (g) Xaa$_{89}$ is T or A; (h) Xaa$_{91}$ is V; (i) Xaa$_{93}$ is F or V; (j) Xaa$_{94}$ is I; (k) Xaa$_{110}$ is G; (l) Xaa$_{114}$ is V or M; (m) Xaa$_{120}$ is S; (n) Xaa$_{128}$ is Y, F, or W; (o) Xaa$_{132}$ is V; and (p) Xaa$_{134}$ is R.

The invention also provides a variant of human BMP7 protein wherein the mature domain of the BMP7 comprises a polypeptide comprising the amino acid sequence of SEQ ID NO: 3 wherein: (a) Xaa$_{33}$ is D; (b) Xaa$_{37}$ is A; (c) Xaa$_{60}$ is E; (d) Xaa$_{65}$ is G; (e) Xaa$_{86}$ is L; (f) Xaa$_{87}$ is V; (g) Xaa$_{89}$ is T or A; (h) Xaa$_{91}$ is V; (i) Xaa$_{93}$ is V; (j) Xaa$_{94}$ is I; (k) Xaa$_{110}$ is G; (l) Xaa$_{114}$ is V or M; (m) Xaa$_{120}$ is S; (n) Xaa$_{128}$ is F or W; (o) Xaa$_{132}$ is V; and (p) Xaa$_{134}$ is R. Preferably, Xaa$_{114}$ is V and Xaa$_{128}$ is W.

The invention further provides a variant of human BMP7 protein wherein the mature domain of the BMP7 protein comprises a F93V/N110G variant as shown in SEQ ID NO:4; a Y65G/I86L/T89A/N110G variant as shown in SEQ ID NO: 5; a Y65G/I86L/N110G/Y128F variant as shown in SEQ ID NO: 6; a Y65G/I86L/N110G/Y128W variant as shown in SEQ ID NO: 7; a Y65G/I86L/F93V/N110G/Y128W variant as shown in SEQ ID NO: 8; a Y65G/T89A/N110G/Y128F variant as shown in SEQ ID NO: 9; a Y65G/I86L/N110G variant as shown in SEQ ID NO: 10; or a Y65G/Y114M variant as shown in SEQ ID NO: 11. More preferably, variants of human BMP7 protein of the present invention comprise a Y65G/I86L/N110G/Y128W variant of the human mature BMP7 protein as shown in SEQ ID NO: 7 or a Y65G/I86L/F93V/N110G/Y128W variant of the human mature BMP7 protein as shown in SEQ ID NO: 8 (hereinafter, referred to as human mature BMP7 protein variant F9 or human mature BMP7 protein variant F9). Even more preferably, the human mature BMP7 protein variant of the present invention comprises human mature BMP7 protein variant F9, which is a Y65G/I86L/F93V/N110G/Y128W variant of the human mature BMP7 (see, SEQ ID NO: 8).

The invention also provides a variant of the human BMP7 protein wherein the mature domain of the BMP7 protein variant comprises the amino acid sequence of SEQ ID NO: 3 wherein:

$Xaa_{33}$ is D or M; $Xaa_{37}$ is A or P; $Xaa_{60}$ is E or Q; $Xaa_{65}$ is Y, S, or G; $Xaa_{86}$ is I, V, or L; $Xaa_{87}$ is V or L; $Xaa_{89}$ is T, S, or A; $Xaa_{91}$ is V or M; $Xaa_{93}$ is F or V; $Xaa_{94}$ is I, F or M; $Xaa_{110}$ is G; $Xaa_{114}$ is V or M; $Xaa_{120}$ is S or Q; $Xaa_{128}$ is Y, F or W; $Xaa_{132}$ is V, Q, or S; and, $Xaa_{134}$ is R or K, and wherein the N-terminus of the variant protein is covalently fused to the C-terminus of the human BMP7 pro-domain sequence of SEQ ID NO: 18.

The invention further provides a variant of human pro-BMP7 protein wherein said protein comprises a polypeptide comprising an amino acid sequence selected from the group consisting of SEQ ID NO: 12; SEQ ID NO: 13; SEQ ID NO: 14; SEQ ID NO: 15; and SEQ ID NO: 16.

The invention further provides a variant of human mature BMP7 protein wherein said variant comprises a polypeptide having the amino acid sequence as shown in SEQ ID NO: 17.

The invention further provides human BMP7 protein variants that have increased specific activity, improved solubility characteristics, improved bioavailability, decreased binding to endogenous circulating inhibitors, and/or reduced EBF activity as compared to the corresponding wild type human BMP7 protein.

Another aspect of the present invention is a pharmaceutical composition comprising a human BMP7 protein variant of the present invention together with a pharmaceutically acceptable carrier, diluents, or excipient and optionally one or more other therapeutic ingredients.

Another aspect of the invention provides methods of treating cancer comprising administering to a patient in need thereof in simultaneous, separate, or sequential combination of an effective amount of a human BMP7 protein variant of the present invention with an effective amount of one or more chemotherapeutic agents or ionizing radiation. Preferably, the methods of treating cancer are methods for treating lung cancer, including, but not limited to, non-small cell lung cancer (NSCLC), brain cancer, cervical cancer, skin cancer, head and neck cancer, glioblastoma, neuroblastoma, or colorectal cancer. Preferably, the human BMP7 protein variant of the present invention is administered to the patient prior to the administration of one or more chemotherapeutic agent(s) and/or ionizing radiation.

An aspect of the invention is the use of a human BMP7 protein variant of the present invention in combination with all-trans retinoic acid (ATRA) for the treatment of cancers in which the retinoid receptors RAR alpha and RAR gamma are known to be important including, but not limited to, lung cancer, brain cancer, cervical cancer, skin cancer, head and neck cancer, glioblastoma, neuroblastoma, oral leukoplakia, oral squamous cell carcinoma, non-small cell lung cancer (NSCLC), breast cancer, ovarian cancer, T-cell lymphoma, soft tissue sarcoma, pancreatic cancer, colorectal cancer, Hodgkin's lymphoma, or non-Hodgkin's lymphoma.

An aspect of the invention is the use of a human BMP7 protein variant comprising a polypeptide having the amino acid sequence of SEQ ID NO: 7 or 8 in combination with ATRA for the treatment of cancers in which the retinoid receptors RAR alpha and RAR gamma are known to be important including, but not limited to, lung cancer, brain cancer, cervical cancer, skin cancer, head and neck cancer, glioblastoma, neuroblastoma, oral leukoplakia, oral squamous cell carcinoma, non-small cell lung cancer (NSCLC), breast cancer, ovarian cancer, T-cell lymphoma, soft tissue sarcoma, pancreatic cancer, colorectal cancer, Hodgkin's lymphoma, or non-Hodgkin's lymphoma.

The human BMP7 protein variants of the present invention may be achieved through generating appropriate gene sequences, i.e. by arranging the appropriate nucleotide sequences and expressing them in a suitable cell line. The desired nucleotide sequences can be produced using a method such as codon-based mutagenesis. Such procedures permit the production of any and all frequencies of amino acid residues at any desired codon positions within an oligonucleotide.

The invention provides a method for treating cancer, cartilage damage and degeneration, pain associated with osteoarthritis, or bone fracture healing comprising administering a therapeutically effective amount of a variant of human BMP7 of the present invention to a human patient in need thereof. Preferably, the invention also provides a method for treating cancer comprising administering a therapeutically effective amount of a variant of human BMP7 of the present invention to a human patient in need thereof wherein said cancer is selected from the group consisting of lung cancer, including, but not limited to, non-small cell lung cancer (NSCLC), brain cancer, cervical cancer, skin cancer, head and neck cancer, glioblastoma, neuroblastoma, and colorectal cancer.

The invention provides a method for treating cancer comprising administering a therapeutically effective amount of a variant of human BMP7 protein of the present invention in combination with all-trans retinoic acid to a patient in need thereof.

The invention provides a variant of human BMP7 protein of the present invention in combination with ATRA for use as a medicament.

The invention provides a variant of human BMP7 protein in combination with ATRA for use in the treatment of cancer said cancer is selected from the group consisting of lung cancer, brain cancer, cervical cancer, skin cancer, head and neck cancer, glioblastoma, neuroblastoma, oral leukoplakia, oral squamous cell carcinoma, non-small cell lung cancer (NSCLC), breast cancer, ovarian cancer, T-cell lymphoma, soft tissue sarcoma, pancreatic cancer, colorectal cancer, Hodgkin's lymphoma, and non-Hodgkin's lymphoma.

The retinoic acid receptor (RAR) is a type of nuclear receptor which is activated by both ATRA and 9-cis retinoic acid. There are three RARs: RAR-alpha, RAR-beta, and RAR-gamma. Activation of the RARs results in a stimulation of alkaline phosphatase activity, which can be measured essentially as described in Example 3.

The invention further provides the use of a variant of human BMP7 protein in combination with ATRA for the manufacture of a medicament for the treatment of cancer.

Another aspect of the present invention provides variants of human BMP7 protein in combination with ATRA for use as a medicament.

Another aspect of the invention embodies a variant of human BMP7 protein in combination with ATRA according to the present invention for use in the treatment of cancer.

The invention provides variants of the human BMP7 protein for use as a medicament.

The invention provides a variant of the human BMP7 protein for use in the treatment of cancer, cartilage damage and degeneration, pain associated with osteoarthritis or bone fracture healing.

The invention further provides the use of a variant of human BMP7 protein of the present invention for the manufacture of a medicament for the treatment of cancer, cartilage damage and degeneration, pain associated with osteoarthritis or bone fracture healing.

Other embodiments of the invention are drawn to polynucleotides encoding the variants of human BMP7 protein of the present invention. Another embodiment is a vector containing said polynucleotide(s) and a host cell carrying said vector. Another embodiment is drawn to processes for producing a human BMP7 protein variant of the present invention by culturing host cells carrying said vector containing DNA encoding said protein, expressing said protein from the host cells and recovering the protein from the culture media.

For purposes of the present invention, as described and claimed herein, terms are defined as follows:

The term "about" means up to a 10% variance of the value such term would be given depending on the number of significant figures. For example, 'about 200' encompasses from 180 to 220 and 'about 1' encompasses from 0.9 to 1.1.

The term "administering" refers to an act to transfer a pharmaceutical composition of the present invention into the body of a mammal, preferably a human, in need thereof.

Administration may be via any route known to be effective by the physician of ordinary skill. Parenteral administration is one form of administration commonly understood in the medical literature as the injection of a dosage form into the body by a sterile syringe or some other mechanical device such as an infusion pump. The parenteral administration may include intravenous injection, subcutaneous injection, muscular injection, intraperitoneal injection, endothelial administration, local administration, intranasal administration, intrapulmonary administration, and rectal administration. Administration at the time of surgery or through the use of x-ray imaging (fluoroscopy) are additional forms.

All-trans retinoic acid (ATRA) is a ligand for both the retinoic acid receptors (RARs) and the retinoid X receptors (RXRs). RARs and RXRs function as ligand inducible transcription factors that regulate the growth and differentiation of both normal and malignant cells (Zhou et al., Phil Trans. R. Soc. B 362: 959-971, 2007).

The term "bone healing" and "bone fracture healing" are used interchangeably herein and are intended to refer to bone repair associated with delayed union and non-union fractures of femoral and tibial bone, fractures of toe and metatarsal bone, proximal humerus bone fractures, other bone fractures, alveolar bone defects associated with dental implant fixtures, intervertebral disc degeneration, spinal fusions, and bone repair associated with cranio-maxillofacial surgeries or enhanced osseous integration to stabilize fixation of implants (screws, plates, prosthesis, dental implants).

Cartilage damage and degeneration refers to cartilage injury resulting from joint injuries associated with trauma, sports, falls, or collisions such as post-traumatic knee cartilage injury from joint dislocation, ligament tear, meniscus tear, post-traumatic shoulder cartilage injury, post-traumatic cartilage injury of the hip, post-traumatic cartilage injury of the elbow, or other cartilage damage such as osteoarthritis.

Pain associated with osteoarthritis refers to pain associated with post-traumatic osteoarthritis, knee osteoarthritic pain, osteochondral defect or related disorders.

Pharmaceutically acceptable excipient refers to a pharmaceutically acceptable formulation carrier, solution, or additive to enhance the formulation characteristics. Such excipients must be compatible with the other ingredients of the formulation and not deleterious to the recipient thereof and are well known to the skilled artisan, see, e.g., Remingtons Pharmaceutical Sciences, 19th Edition, Mack Publishing Company, 1995.

A stable formulation is one in which the protein remains soluble for an extended period of time under the conditions of storage.

Sulfated polysaccharides are compounds consisting of two or more saccharide units containing one or more sulfation sites per saccharide unit. Exemplary sulfated polysaccharides include heparin, heparin sulfate, dextran sulfate, sucrose octasulfate, sulfated β-cyclodextrin, myo-inositol hexasulfate, polypentosan sulfate, fucoidan, chonroitin sulfate A, chonroitin sulfate B, chonroitin sulfate C, and derivatives thereof.

Potency or specific activity is a measurement of the relative activity of variants of human BMP7 protein including those of the present invention and may be measured in the MFc7 cell assay described hereinbelow in Example 5, for example. Generally, the relative activity is compared to the wild type human mature BMP7 to yield a relative potency for the human BMP7 protein variant.

Soluble or solubility refers to the reduction or relative absence of aggregated protein that is determined by an aggregation assay such as the one described herein in Example 6. Solubility is also a measure of the physical stability of the BMP7 protein variant which may be measured in a thermal unfolding assay essentially as described in Example 7.

The terms "subject", "patient", or "individual", are used interchangeably herein, and all of them refer to a mammal, including, but not limited to, murines, simians, humans, mammalian farm animals (i.e., sheep, etc.), mammalian sport animals (i.e., horses), and mammalian pets (i.e., dogs or cats); preferably, the term refers to humans. In a certain embodiment, the subject, preferably a human, is further characterized with a disease or disorder or condition that would benefit from treatment with a variant of human BMP7 protein of the present invention.

Treating as used herein describes the management and care of a patient for the purpose of combating a disease, condition, or disorder and includes the administration of a pharmaceutical composition of the present invention to alleviate the symptoms or complications, or eliminate the disease, condition, or disorder.

The phrase "therapeutically effective amount" refers to the amount of an active agent necessary to impart a therapeutic benefit to a patient.

A therapeutically effective amount is the amount of an active agent necessary to impart a therapeutic benefit to a patient. For example, a therapeutically effective amount administered to a human patient in need of treatment for cartilage damage and degeneration, pain associated with osteoarthritis, or bone healing is such an amount which induces, ameliorates, or otherwise causes an improvement in the pathological symptoms, disease progression, or physiological conditions associated with cartilage damage and degeneration, pain associated with osteoarthritis, or bone repair/healing. Furthermore, a therapeutically effective amount of a human BMP7 protein variant of the present invention is an amount administered to a human patient in need of treatment for cancer is an amount which in mammals, preferably, humans, reduces the number of cancer cells; reduces the tumor size; inhibits (i.e., slow to some extent or stop) cancer cell infiltration into peripheral tissues organs; inhibit (i.e., slow to some extent or stop) tumor metastasis; inhibits, to some extent, tumor growth; and/or relieves to some extent one or more of the symptoms associated with the cancer. An effective amount of a human BMP7 protein variant of the invention may be administered in a single dose or in multiple doses. Furthermore, an effective amount of a human BMP7 protein variant of the invention may be administered in multiple doses of amounts that would be less than an effective amount if not administered more than once.

As is well known in the medical arts, dosages for any one subject depends upon many factors, including the patient's size, body surface area, age, the particular compound to be administered, gender, time and route of administration, general health, and other drugs being administered concurrently. Dose may further vary depending on the type and severity of the disease. A typical dose of a human BMP7 protein variant of the present invention can be, for example, in the range of about 10 mg to about 1000 mg; preferably, about 50 mg to about 500 mg; more preferably, about 200 mg to about 500 mg; even more preferably, about 200 mg to about 400 mg, even more preferably, about 200 mg to about 300 mg; even more preferably, about 225 mg to about 275 mg; even more preferably, about 250 mg to about 275 mg; however, doses below or above this exemplary range are envisioned, especially considering the aforementioned factors. A daily parenteral dosage regimen can be from about 250 µg/kg to about 10 mg/kg. Progress may be monitored by periodic assessment, and the dose adjusted accordingly.

In some embodiments of the present invention, a single dose of a human BMP7 protein of the present invention may be administered intravenously for treating a cancer in an adult patient. A typical single dose for intravenous administration of a variant of human BMP7 protein of the present invention can be, for example, in the range of about 10 mg to about 1000 mg; preferably, about 10 mg to about 500 mg; more preferably, about 10 mg to about 500 mg; more preferably, about 10 mg to about 400 mg; more preferably, about 10 mg to about 350 mg; more preferably, about 10 mg to about 300 mg; even more preferably, about 10 mg to about 275 mg; even more preferably, about 10 mg to about 250 mg; even more preferably, about 10 mg to about 200 mg; even more preferably, about 10 mg to about 175 mg; even more preferably, about 10 mg to about 150 mg; or most preferably, about 10 mg to about 125 mg; however, doses below or above this exemplary range are envisioned, especially considering the aforementioned factors. Alternatively, a typical single dose for intravenous administration of a variant of human BMP7 protein of the present invention can be, for example, from about 0.2 mg/kg to about 15 mg/kg body weight; more preferably, about 0.2 mg/kg to about 10 mg/kg; even more preferably, about 0.2 mg/kg to about 7.5 mg/kg; even more preferably, about 0.2 mg/kg to about 5 mg/kg; even more preferably, about 0.2 mg/kg to about 4 mg/kg; even more preferably, about 0.2 mg/kg to about 3 mg/kg; even more preferably about 0.2 mg/kg to about 2.5 mg/kg; or most preferably, about 0.2 mg/kg to about 2 mg/kg. Such doses can be administered intravenously once every week, once every two weeks, once every three weeks, or once every month, for example. Progress may be monitored by periodic assessment, and the dose adjusted accordingly.

These suggested amounts of a variant of human BMP7 protein of the present invention are subject to a great deal of therapeutic discretion. The key factor in selecting an appropriate dose and scheduling is the result obtained. Factors for consideration in this context include the particular disorder being treated, the clinical condition of the individual patient, the cause of the disorder, the site of delivery of the protein, the particular type of form of the protein (e.g., pro-BMP7 protein variant or mature BMP7 protein variant) the method of administration, the scheduling of administration, and other factors known to medical practitioners.

Human BMP7 protein is a secreted signaling molecule of the TGF-beta superfamily and was originally identified for its ability to induce bone formation but later became recognized as a multifunctional cytokine which mediates growth and differentiation of many different cell types. Human BMP7 protein is expressed in cells as a 292 amino acid precursor protein and the mature, biologically active BMP7 is generated by proteolytic removal of the signal peptide and pro-peptide. The wild type human BMP7 protein amino acid sequence containing the signal peptide (the first 29 amino acids), pro-domain, and mature peptide (underlined) is indicated as SEQ ID NO: 1

```
                                              (SEQ ID NO: 1)
MHVRSLRAAAPHSFVALWAPLFLLRSALADFSLDNEVHSSFIHRRLRSQE

RREMQREILSILGLPHRPRPHLQGKHNSAPMFMLDLYNAMAVEEGGGPGG

QGFSYPYKAVFSTQGPPLASLQDSHFLTDADMVMSFVNLVEHDKEFFHPR

YFIHREFRFDLSKIPEGEAVTAAEFRIYKDYIRERFDNETFRISVYQVLQ

EHLGRESDLFLLDSRTLWASEEGWLVFDITATSNHWVVNPRHNLGLQLSV

ETLDGQSINPKLAGLIGRHGPQNKQPFMVAFFKATEVHFRSIRSTGSKQR

SQNRSKTPKNQEALRMANVAENSSSDQRQACKKHELYVSFRDLGWQDWII

APEGYAAYYCEGECAFPLNSYMNATNHAIVQTLVHFINPETVPKPCCAPT

QLNAISVLYFDDSSNVILKKYRNMVVRACGCH.
```

It is understood by the skilled artisan that the signal peptide may be removed by proteolytic cleavage resulting in an intact pro-domain/mature peptide that is designated as pro-BMP7.

Wild type human mature BMP7 is a dimer of two glycosylated, 139 amino acid disulfide-linked, homodimeric proteins of about 35 kDa. Each homodimeric protein has the amino acid sequence as shown in SEQ ID NO: 2:

```
                                              (SEQ ID NO: 2)
STGSKQRSQNRSKTPKNQEALRMANVAENSSSDQRQACKKHELYVSFRDL

GWQDWIIAPEGYAAYYCEGECAFPLNSYMNATNHAIVQTLVHFINPETVP

KPCCAPTQLNAISVLYFDDSSNVILKKYRNMVVRACGCH.
```

The variants of human BMP7 protein of the present invention include variants of human mature BMP7 of SEQ ID NO: 2, with the specific amino acid positions changed indicated in the consensus sequence as shown in SEQ ID NO: 3. Particular variants of human mature BMP7 protein of the present invention have increased specific activity, improved solubility characteristics, improved bioavailability, decreased binding to endogenous circulating inhibitors, and/or reduced EBF activity compared to the wild type mature human BMP7 protein.

Preferred variants of human BMP7 protein are selected from the group consisting of F93V/N110G SEQ ID NO: 4; Y65G/I86L/T89A/N110G SEQ ID NO: 5; Y65G/I86L/N110G/Y128F SEQ ID NO: 6; Y65G/I86L/N110G/Y128W SEQ ID NO:7; Y65G/I86L/F93V/N110G/Y128W SEQ ID NO: 8, Y65G/T89A/N110G/Y128F SEQ ID NO: 9; Y65G/I86L/N110G SEQ ID NO: 10; and, Y65G/V114M SEQ ID NO: 11. The most preferred variants of BMP7 of the present invention are selected from the group consisting of Y65G/I86L/N110G/Y128W (SEQ ID NO: 7) and Y65G/I86L/F93V/N110G/Y128W (SEQ ID NO: 8).

The present invention also provides variants of human pre-BMP7 (i.e., SEQ ID NO: 1) as well as variants of human pro-BMP7 (i.e., SEQ ID NO: 21). Preferred variants of human pro-BMP7 of the present invention that contain the pro-domain fused to the N-terminus of the human mature BMP7 protein variant are selected from the group consisting of SEQ ID NO: 12; SEQ ID NO: 13; SEQ ID NO:14; SEQ ID NO: 15; and SEQ ID NO: 16.

The variants of human BMP7 protein of the present invention may be synthesized by recombinant organisms engineered using methods well known in the art, or alternatively, by chemical synthesis. Accordingly, other embodiments of the invention are directed to polynucleotides encoding the variants of human BMP7 protein. Another embodiment is a vector containing said polynucleotide and a host cell carrying said vector. Another embodiment is directed to processes for producing a protein by culturing host cells carrying said vector containing DNA encoding said protein, expressing said protein from the host cells and recovering the protein from the culture media.

The polynucleotides that encode for a variant of human BMP7 of the present invention may include the following: only the coding sequence for the human mature BMP7 protein variant, the coding sequence for the variant and additional coding sequence such as a functional protein, or a signal or secretory sequence or a pro-domain sequence; the coding sequence for the human mature BMP7 protein variant and non-coding sequence, such as introns or non-coding sequence 5' and/or 3' of the coding sequence for the variant. Thus, the term "polynucleotide encoding a variant" encompasses a polynucleotide that may include not only the coding sequence for the human mature BMP7 protein variant but also a polynucleotide which includes additional coding and/or non-coding sequence. It is known in the art that a polynucleotide sequence that is optimized for a specific host cell/expression system can readily be obtained from the amino acid sequence of the desired protein. Examples of polynucleotides of the present invention are SEQ ID NO: 19 and SEQ ID NO: 20 which are DNA sequences that encode pre-BMP7 forms of the human mature BMP7 protein variants as shown in SEQ ID NO: 7 and SEQ ID NO: 8 respectively.

The polynucleotides of the present invention are expressed in a host cell after the sequences have been operably linked to an expression control sequence. These expression vectors are typically replicable in the host organisms either as episomes or as an integral part of the host chromosomal DNA. Commonly, expression vectors contain selection markers, e.g., tetracycline, neomycin, and/or dihydrofolate reductase, to permit detection of those cells transformed with the desired DNA sequences. The vectors containing the polynucleotide sequences of interest (e.g., the variants of BMP7 protein and expression control sequences) are transferred into a host cell by well-known methods, which vary depending on the type of cellular host.

The variants of human BMP7 protein of the present invention may readily be produced in mammalian cells such as CHO, NS0, HEK293 or COS cells, in bacterial cells such as E. coli or Pseudomonas flourescence or in fungal or yeast cells. Preferably, the host cell is a mammalian cell. The preferred mammalian cell is a CHO cell. The host cells are cultured using techniques well known in the art.

In one embodiment the present invention relates to a vector containing and expressing in a host a pre-BMP7 gene, a pro-BMP7 gene or a mature BMP7 gene. The BMP7 gene encoding the pre-BMP7 protein, the pro-BMP7 protein or the mature BMP7 protein may originate from a mammal. In a preferred embodiment, the expression vector may comprise a polynucleotide that encodes a variant of a human pre-BMP7, a variant of a human pro-BMP7 or a variant of a human mature BMP7 protein. The polynucleotide encoding these human BMP7 protein variants may be operatively linked to a promoter and optionally to an enhancer.

In some embodiments, the invention relates to a mammalian host cell harboring a vector comprising a polynucleotide encoding a human pre-BMP7 protein variant, a human pro-BMP7 protein variant, or a human mature BMP7 protein variant, wherein the pro-BMP7 protein variant is deleted of the "pre" or "signal" peptide at the N-terminus. Preferably, the mammalian host cell harbors a vector that comprises a polynucleotide that encodes for the expression of a human mature BMP7 protein variant having the amino acid sequence of any one of SEQ ID NO: 3-11, or a pre- or pro-form thereof. More preferably, the mammalian host cell harbors a vector that comprises a polynucleotide that encodes for the expression of a human pro-BMP7 protein variant having the amino acid sequence of any one of SEQ ID NO: 12-16, or a pre-form thereof. In some embodiments a "pre" or "signal" peptide sequence from a different origin is fused to the N-terminus of the human pro-BMP7 protein variant. In some embodiments of the present invention, the "pre" or "signal" peptide sequence may be the insulin-like growth factor 1 (IGF-1) or the tissue plasminogen activator (tPA) peptide signal sequence, for example.

Various methods of protein purification may be employed and such methods are known in the art and described, for example, in Protein Purification: Principals, High Resolution Methods, and Applications, 2nd Edition, Wiley-VCH Inc. (Germany, 1998).

Pharmaceutical compositions of the present invention can be prepared using conventional dissolution and mixing procedures. One of ordinary skill in the formulation sciences will recognize that the order of addition of a medically useful protein, osmolyte, and hydrophobic preservative, can be varied without compromising the effectiveness of the formulation. To further improve the bioavailability of the pharmaceutical compositions of the present invention, targeting strategies may be employed for the retention of the human BMP7 protein variants in the joint space. This involves the formulation in lactose buffer or encapsulation techniques to physically entrap molecules in the joint space (e.g. hydrogel, nanoparticles, liposomes) or targeting to proteins in the extracellular space that include but are not limited to collagens (type I and II) or integrins. For bone healing, the human BMP7 protein variant of the present invention may be mixed with carriers such as collagen type 1.

Hydrophobic preservative refers to a hydrophobic compound that may be added to a pharmaceutical formulation to act as an anti-microbial agent. Examples of hydrophobic preservatives acceptable in parenteral formulations are alkylparabens, phenolic preservatives i.e. phenol and cresol, benzyl alcohol, chlorobutanol, benzoic acid, and various mixtures thereof.

Reference to a wild type human BMP7 protein or variant thereof herein, including by reference to a SEQ ID NO: or a unique reference code (for example, "F9") refers to a homodimer thereof. As a non-limiting example, "human mature BMP7 protein variant F9 (SEQ ID NO: 8)" or interchangeably "BMP7 protein variant F9" or the like, as used herein, refers to a homodimer wherein each monomeric subunit has the sequence as shown in SEQ ID NO: 8 and the subunits are linked via disulfide bond(s).

For the functional assays described hereinbelow, treatment with or administration of a particular pro-BMP7 protein or a variant thereof to, refers to treatment with or administration of homodimers of the particular human mature BMP7, i.e., either wild type or a variant thereof, which are generally in a non-covalent complex with wild type human pro-domain.

Cresol refers to meta-cresol, ortho-cresol, para-cresol, chloro-cresol, or mixtures thereof.

Isotonicity agent refers to a compound that is tolerated physiologically and imparts a suitable tonicity to a formulation to prevent the net flow of water across cell membranes. Examples of isotonicity agents are glycerin, salts e.g. NaCl, KCl, and sugars, e.g. dextrose, mannitol, and sucrose.

Osmolytes are compounds that have the ability to stabilize proteins against denaturation and aggregation. Exemplary osmolytes include amino acids, polyols (e.g. sorbitol, mannitol, xylitol, and glycerol), sugars, sugar alcohols, sugar acids and the like. Preferred osmolytes include histidine, salts of histidine, glycine, salts of aspartic acid, salts of glutamic acid, salts of lysine, salts of arginine, serine, proline and alanine. The preferred osmolyte is arginine. Preferably, the concentration of arginine will be about 100 mM to 1 M; more preferably about 125 mM to about 800 mM; still more preferably about 200 mM to about 500 mM; and, most preferably about 250 mM.

The preferred hydrophobic preservative is selected from the group consisting of phenol, m-cresol, methylparaben, propylparaben, benzyl alcohol, chlorocresol, and mixtures thereof.

The pharmaceutical compositions of the present invention optionally may contain other compounds in addition to the medically useful protein, hydrophobic preservative, and osmolyte. For example, pharmaceutically acceptable surfactants like Tween 20 (polyoxyethelene (20) sorbitan monolaurate), Tween 40 (polyoxyethelene (20) sorbitan monopalmitate), Tween 80 (polyoxyethelene (20) sorbitan monooleate), Pluronic F68 (polyoxyethelene polyoxypropylene glycol), and PEG (polyethylene glycol) may optionally be added to the formulation to reduce aggregation. These additives are particularly useful if a pump or plastic container is used to administer the formulation. A pharmaceutically acceptable surfactant may further reduce protein aggregation.

The pharmaceutical composition of the present invention may contain a sulfated polysaccharide. The preferred sulfated polysaccharide is selected from the group consisting of heparin, heparin sulfate, and dextran sulfate.

The pharmaceutical composition of the present invention may contain an aqueous buffer. The buffers suitable for the present invention are those having pH buffering capacity in the range of from about pH 6 to about pH 8 and are compatible with the dried protein. The pH of the formulation solution is about 6.5 to about 7.5. More preferably, 6.8 to about 7.5. Still more preferably, a pH between about 7.0 and about 7.4.

Representative buffer systems to maintain effective pH control include Tris-acetate, sodium citrate, potassium citrate, citrate-glycine and sodium phosphate. More preferred buffer systems include sodium citrate and sodium phosphate. The most preferred buffer is sodium citrate. The preferred concentration of the buffer system is about 1 mM to about 50 mM. A more preferred concentration is about 5 mM to about 30 mM. The most preferred concentration is about 10 mM. The skilled artisan will recognize that many other buffer systems are available which also can be used to maintain the pH in the preferred range.

In addition, an isotonicity agent, preferably NaCl or KCl, may be optionally added to the soluble, pharmaceutical composition/formulation. Most preferably the isotonicity agent is NaCl. The concentration of the isotonicity agent is in the range known in the art for parenteral formulations, preferably about 100 mM to about 250 mM, more preferably about 125 mM to about 200 mM and still more preferably about 150 mM.

The pharmaceutical compositions of the human BMP7 protein variants of the present invention may be administered by any means known in the art that achieve the generally intended purpose of treatment for cancer, cartilage damage and degeneration, pain associated with osteoarthritis, or bone healing.

The preferred route of administration is parenteral, defined herein as referring to modes of administration that include but are not limited to intra-articular, intravenous, intramuscular, intraperitoneal, subcutaneous injection and infusion. Most preferably, the parenteral administration of the human BMP7 protein variants of the present invention is by intra-articular administration in the joint space for cartilage repair or the OA pain indications.

The dosage administered will be dependent upon the age, health, and weight of the recipient, kind of concurrent treatment, if any, frequency of treatment, and the nature of the of the effect desired. Typical dosage levels can be optimized using standard clinical techniques and will be dependent on the mode of administration and the condition of the patient.

Thus, an embodiment of the present invention is a method of treatment for cartilage damage and degeneration, pain associated with osteoarthritis, or bone healing in a subject in need thereof by administering a therapeutically effective amount of a variant of human BMP7 protein of the present invention. The subject is a mammal, preferably a human.

Another embodiment of the present invention is a method of treatment for cartilage damage and degeneration or pain associated with osteoarthritis in a mammal in need thereof comprising the administration of a therapeutically effective amount of a variant of human BMP7 of the present invention wherein said mammal is selected from the group consisting of human, dog, equine, feline or sheep.

Another embodiment of the present invention is a method of treatment for bone healing in a mammal in need thereof comprising the administration of a therapeutically effective amount of a variant of human BMP7 of the present invention, wherein said mammal is selected from the group consisting of human, dog, equine, feline or sheep.

Having now described the present invention in detail, the same will be more clearly understood by reference to the following Examples, which are included herewith for pur-

Abbreviations (not an Exhaustive List)

ATRA: All-trans retinoic acid
BMP7: Bone morphogenetic protein 7
DMSO: Dimethyl sulfoxide
EGF: Epidermal Growth Factor
PBS: Phosphate-buffered saline
PNPP: p-Nitro-phenyl phosphate, disodium salt
VEGF: Vascular endothelial growth factor
WT: wild type

EXAMPLE 1

Expression Methods

The human BMP7 proteins and variants of human BMP7 proteins of the present invention may be produced by culturing a host cell transformed with an expression vector containing a nucleic acid encoding a human BMP7 protein or variant thereof, under the appropriate conditions to induce or cause expression of the human BMP7 protein or variant thereof. Either transient or stable transfection methods may be used. The conditions appropriate for expression of BMP7 proteins or variants thereof may vary with the choice of the expression vector and the host cell, and may be ascertained by one skilled in the art through routine experimentation.

EXAMPLE 2

Stimulation of RAR Alpha and RAR Gamma by BMP7

3T3-L1 fibroblasts and MFc7 mouse renal myofibroblasts may be maintained under routine cell culture conditions in DMEM/10% calf serum medium or OPTI-MEM/10% FBS medium, respectively. The cells may be plated in 10 cm tissue culture plates at a seeding density of 500,000 cells/plate. After 48 hours, the cells may be washed with PBS prior to the addition of either DMEM/2% dialyzed FBS or OPTI-MEM/2% dialyzed FBS medium containing 1 µg/mL human BMP7 protein or 1 µg/mL of a human BMP7 protein variant. The cells may be incubated for 48 hours and then rinsed with ice-cold PBS, and then lysed with Protein Extraction Reagent. Then lysates may be centrifuged at 14,000×g for 15 minutes. A Bradford protein assay may be performed to determine the protein concentration of each lysate. Equivalent amounts of protein (for example, 25 µg) may be resolved by SDS-PAGE and then transferred to nitrocellulose membranes for Western Blot analysis. The membranes may be probed with an anti-RAR alpha antibody and/or an anti-RAR gamma antibody.

In experiments conducted essentially as described above in this Example 2, the intensity of the Western Blots demonstrated that with both MFc7 and 3T3-L1 cell lines, human BMP7 protein and human BMP7 protein variants, including human BMP7 protein variant F9, stimulated RAR alpha and RAR gamma protein expression (data not shown). Accordingly, RAR-alpha and RAR-gamma appear to be involved in a major signaling pathway for BMP7.

EXAMPLE 3

Combination Treatment with Human BMP7 Proteins and ATRA in 3T3-L1 and MFc7 Cells 3T3-L1 fibroblasts and MFc7 mouse renal myofibroblasts may be grown essentially as described in Example 2 above. After 48 hours the cells may be washed with PBS prior to the addition of either DMEM/2% dialyzed FBS or OPTI-MEM/2% dialyzed FBS medium containing control vehicle, 1 µg/ml human proBMP7 protein, 1 µM ATRA or a combination of both human BMP7 protein (1 µg/ml) and ATRA (1 µM) may be added for 48 hours. After treatment the cells may be rinsed with PBS and stored at −80° C. for approximately 20 minutes. The cells may be thawed at 37° C. for 30 minutes and 100 µl of PNPP may be added to every well. The plate may be incubated at 37° C. for 1 hour. The absorbance at 405 nm may be read on a plate reader.

In experiments conducted essentially as described above in this Example 3, the combination treatment of wild type human pro-BMP7 protein and ATRA resulted in a synergistic stimulation of alkaline phosphatase. The data shown in Table 1 represent the fold change in alkaline phosphatase stimulation relative to control vehicle treated cells.

TABLE 1

| Treatment | 3T3-L1 | MFc7 |
|---|---|---|
| Control | 1.0 | 1 |
| Wild type human pro-BMP7 | 1.2 | 21 |
| ATRA | 2.9 | 8 |
| COMBO | 12.4 | 103 |

EXAMPLE 4

SOX2 and Ki67 Expression in GBM Cells Treated with a Human BMP7 Protein Variant in Combination with ATRA SOX2 is a transcription factor expressed by neural stem cells. Its expression is lost when a cell differentiates. Therefore, SOX2 is considered to be a marker for terminal differentiation of multipotent brain tumor cells.

Ki67 is a nuclear protein expressed in proliferating cells. It is preferentially expressed in late G1, S, G2 and M-phase of the cell cycle, and G0 or quiescent cells are negative for this protein. Fast growing cell lines have a high percentage of Ki67 positive cells. Ki67 expression is reduced or lost as cells differentiate to indicate that growth is slowing down as the cell population becomes terminally differentiated.

Preparation of Glioblastoma Stem Cell Culture:

Glioblastoma multiforme stem cells (GBMs) may be obtained from patients with primitive brain tumors undergoing complete or partial surgical resection. These cells may be maintained as neurospheres in defined media with 3.34 g/L of DMEM and 2.66 g/L F12 reconstituted in sterile distilled water and containing 1% glucose, 0.12% sodium bicarbonate, 5 mM hepes, 2 mM L-glutamine, 4 mg/L heparin, 10 ng/mL bFGF, 20 ng/mL EGF, 0.4% BSA, 100 µg/mL apotransferrin, 25 µg/mL insulin, 60 uM putrescine, 30 nM sodium selenite, and 20 nM progesterone. Cells may be cultured at 37° C. in 5% $CO_2$. Cells may be plated by enzymatically dispersing spheres into single cells with a 2-5 minute incubation at 37° C. with TrypLE™ Express cell dissociation enzyme. The enzyme may be quenched with Dulbecco's Phosphate Buffered Saline (DPBS) containing Ca+ and Mg+. Then the cells may centrifuged to remove TrypLE and DPBS and resuspended as single cells in defined media and counted by a Coulter Z2 Cell and Particle counter.

Experimental Procedure:

Single GBM cells may be plated in defined media at $2 \times 10^6$ cells/15 mL/T75 flask for high content imaging or $5 \times 10^5$ cells/2 mL/well in 6-well plates for light microscopy. Cells may be treated with 0.01% DMSO, 1 µg/mL ATRA, 100 ng/mL of a human BMP7 protein variant of the present invention (e.g., human BMP7 protein variant F9 (SEQ ID NO: 8)), or a combination of 1 µg/mL ATRA and 100 ng/mL human BMP7 protein variant of the present invention. For light microscopy imaging of the effect of control BMPs (BMP2 and BMP4), cells may be plated as above in 6-well dishes and treated with 0.01% DMSO, 1 µg/mL ATRA, 100 ng/mL BMP2, 50 ng/mL BMP4, or a combination of BMPs at the same concentrations plus 1 µg/mL ATRA. Example images may be captured at 3, 7, and 30 days post-treatment on a Leica DMIRM inverted microscope using a 20× objective, for example. For growth longer than 7 days, media and treatment may be changed approximately every 10 days beginning at day 10.

After collecting medium containing floating neurospheres for each condition, the spheres may be pelleted and incubated with TrypLE to disperse to single cells as described in Preparation 2 while attached cells for each condition may be detached using TrypLE and are then added back to the dispersed neurospheres. Cells may be plated into poly-D-lysine coated 96-well plates at a density of 5,000-10,000 cells/well in 100 µL defined media. Cells may be treated again with 0.01% DMSO, ATRA, human BMP7 protein, or a combination of the two as above, and incubated for an additional 48 hours at 37° C. in 5% $CO_2$. Cells may be fixed with 3.7% formaldehyde for approximately 20 minutes. All dilutions and washes may be performed in PBS. Cells may be permeabilized with 0.1% Triton X-100 (polyethylene glycol octylphenyl ether) for approximately 10 minutes at 25° C. and then washed. Cells may be blocked for 1 hour in 1% bovine serum albumin (BSA) then incubated overnight with 2 µg/mL of a mouse monoclonal anti-SOX-2 antibody in 1% BSA or rabbit monoclonal anti-Ki67 diluted 1:500 in 1% BSA. Cells may be washed further (e.g., two times) then incubated for approximately one hour with goat α-mouse-Alexa-488 IgG or goat α-rabbit-Alexa-488 IgG and 200 ng/mL Hoechst 33342 diluted in 1% BSA solution. Cells may be washed again (e.g., two times) and cell images may be captured using an ArrayScan Vti (Cellomics, Pittsburgh, Pa.) using a 10× objective. Two-channel analysis may be performed with the Target Activation Bioapplication.

In experiments conducted essentially as described above in this Example 4, GBM cells (1000-2000 cells measured per condition) were treated with either control vehicle, human pro-BMP7 protein variant alone, ATRA alone or a combination of human pro-BMP7 protein variant and ATRA. Values were normalized to vehicle control and reflect percent responders of a population. The data summarized in Table 2 represent the treatment of two different clones of GBM cells, CL-61 and CL-1. Briefly summarized, at Day 3, a clear synergistic effect was observed in CL-61 with the combination treatment of human pro-BMP7 protein variant F9 and ATRA with both the SOX2 and the Ki67 markers, indicating that the GBM stem cells are in a terminally differentiated, benign state. A similar synergistic effect was observed with the SOX2 marker on CL-1, but at the 25 day readout instead of Day 3 as seen with C61. These data illustrate the growth variability and differential response to differentiation agents of GBM stem cells, but more importantly, show surprising synergistic effects of the combination treatment of human BMP7 protein variant F9 and ATRA on biomarkers of terminal differentiation of multipotent brain tumor cells.

TABLE 2

|  |  | CL-61 Day 0 | CL-1 Day 3 | Cl-1 Day 25 |
| --- | --- | --- | --- | --- |
| SOX2 | Control vehicle | 100 | 100 | 100 |
|  | ATRA (1 µg/ml) | 89 | 97 | 97 |
|  | Pro-BMP7 variant F9 (100 ng/mL) | 84 | 100 | 72 |
|  | Combination | 19 | 94 | 38 |
| Ki67 | Control vehicle | 100 | 100 | 100 |
|  | ATRA (1 µg/ml) | 83 | 99 | 101 |
|  | Pro-BMP7 variant F9 (100 ng/mL) | 69 | 88 | 78 |
|  | Combination | 39 | 66 | 76 |

Surprisingly, the combination of a variant of human pro-BMP7 protein (i.e., F9) with ATRA produced significant synergy with regard to loss of SOX2 as indicated in the treatment of glioblastoma stem cells.

EXAMPLE 5

Characterization of BMP7 Protein Variants Using the MFc7 Bioassay

MFc7 mouse renal myofibroblasts (mouse kidney fibroblast cell line) may be maintained under routine cell culture conditions in OPTI-MEM/10% FBS medium. The cells may be plated in 10 cm tissue culture plates at a seeding density of 500,000 cells/plate. After approximately 48 hours, the cells may be washed with phosphate buffered saline (PBS) prior to the addition of OPTI-MEM/2% dialyzed fetal bovine serum (FBS) medium containing 1 µg/ml BMP7 protein or 1 µg/ml of a BMP7 protein variant and incubated for 48 hours. After treatment the cells may be rinsed with PBS and stored at −80° C. for 20 minutes. After thawing the cells at 37° C. for 30 minutes 100 µl of para-nitrophenyl phosphate (PNPP) may be added. The plate may be incubated at 37° C. for 1 hour. The absorbance at 405 nm may be read utilizing a plate reader. The average relative potency ($EC_{50}$ of wild type BMP7 protein/$EC_{50}$ of the BMP7 protein variant) of certain human BMP7 protein variants of the present invention may be calculated based on such readings.

In experiments conducted essentially as described above in this Example 5, various human BMP7 protein variants of the present invention have an increased average relative potency or specific activity relative to the corresponding wild type human BMP7 protein. More specifically, the increases in average relative potency or specific activity relative to wild type human BMP7 for various human BMP7 protein variants with multiple amino acid position changes are provided in Table 3 while Table 4 provides the same for various human BMP7 protein variants with a single amino acid position change. These data demonstrate that certain human BMP7 protein variants of the present invention have an increased average relative potency or specific activity relative to the corresponding wild type human BMP7 protein.

TABLE 3

| Human BMP7 protein variant | SEQ ID NO: | Name of Human BMP7 protein | Average Relative Potency |
|---|---|---|---|
| F93V/N110G | SEQ ID NO: 4 | | 9 |
| Y65G/I86L/T89A/N110G | SEQ ID NO: 5 | | 10 |
| Y65G/I86L/N110G/Y128F | SEQ ID NO: 6 | | 7 |
| Y65G/I86L/N110G/Y128W | SEQ ID NO: 7 | | 16 |
| Y65G/I86L/F93V/N110G/Y128W | SEQ ID NO: 8 | F9 | 69 |
| Y65G/T89A/N110G/Y128F | SEQ ID NO: 9 | | 6.2 |
| Y65G/I86L/N110G | SEQ ID NO: 10 | | 8.7 |
| Y65G/V114M | SEQ ID NO: 11 | | 5.0 |

TABLE 4

| Human BMP7 protein variant (SEQ ID NO: 2 having the single amino acid mutation shown here) | Average Relative Potency |
|---|---|
| D33M | 3.3 |
| A37P | 7.5 |
| E60Q | 5.5 |
| Y65G | 1.3 |
| I86L | 5.9 |
| I86V | 17.4 |
| T89A | 3 |
| V91M | 3.3 |
| F93V | 16 |
| I94F | 7.5 |
| N110G | 1.7 |
| V114M | 9.4 |

EXAMPLE 6

Solubility Assay for Human BMP7 Protein and Human BMP7 Protein Variants

Solubility/physical stability of human BMP7 protein and human BMP7 protein variants may be measured in a stir-induced aggregation assay. Proteins are diluted to 40 µg/mL with assay buffer (50 mM sodium phosphate, 150 mM NaCl, pH 7.4) to a total volume of 2 mL. This solution may be put in a 7 mL glass vial containing one 'flea' stir bar and stirred at 400-rpm at room temperature. At periodic intervals (typically 0, 30, 60, 90, 120, and 150 minutes) a 150 µL aliquot may be withdrawn and centrifuged for 2 minutes at 16,000×g in a 1.5 mL tube. The supernatant (120 µL) may be transferred to an HPLC vial and the amount of remaining protein may be determined by reversed-phase HPLC under the following conditions: Zorbax C8 SB-300® column (3.5 micron, 4.6×50 mm), mobile phase: A buffer=0.1% TFA (v/v) in water, B buffer=0.085% TFA (v/v) in acetonitrile; flow rate at 1 mL/minute; column heated to 60° C.; autosampler cooled to 10° C., 214 nm UV detection, 80 µL injection, and 20 minute run time using the linear gradient indicated below. From the HPLC chromatograms (not shown) the protein peak or peaks (e.g., mature and pro domains) are integrated and percent change from initial peak area may be calculated.

As shown in Table 5 below, wild type human mature BMP7 is insoluble from the initiation of the assay. In contrast, the human mature BMP7 protein variant F9 (i.e., SEQ ID NO: 8) is significantly more soluble, even at the 150 minute time point. Thus, the BMP7 protein variant F9 (i.e., SEQ ID NO: 8) provides significantly improved solubility relative to wild type mature BMP7.

TABLE 5

Aggregation Assay: Percent of Material Precipitated

| Time (minutes) | Wild type human pro-BMP7 | Human pro-BMP7 Variant F9 | Human mature BMP7 WT (SEQ ID NO: 2) | Human mature BMP7 protein variant (SEQ ID NO: 8) |
|---|---|---|---|---|
| 0 | 0 | 0 | 100 | 0 |
| 30 | 8 | 9 | 100 | 7 |
| 60 | 42 | 23 | 100 | 23 |
| 90 | 51 | 36 | 100 | 24 |
| 120 | 65 | 43 | 100 | 37 |
| 150 | 72 | 55 | 100 | 39 |

EXAMPLE 7

Thermal Unfolding Assay

The effect of temperature on the conformational stability of human BMP7 protein variants may be followed by circular dichroism (CD) on a Jasco J-810 instrument equipped with a thermoelectric sample compartment. Briefly stated, 0.2-1.0 mg/mL pro-BMP7 may be formulated in storage buffer (10 mM citrate, 300 mM NaCl, pH 7.4) and loaded into a 0.02 cm path-length CD cuvette. The sample may be heated from 20 to 80° C. at a linear rate of 1° C./minute and the resulting CD signal at 208 nm may be recorded every 0.2° C. using a 1 second signal response time. A non-linear fit to equation 1 may be performed by the program JMP (SAS Institute Inc, Cary, N.C.) to obtain the thermal unfolding mid-point (Tm).

$$\frac{(Yu + Mu*T)*\mathrm{Exp}[-[(Hm-T*S)/(1.987*T)]] + Yf + Mf*T}{1 + \mathrm{Exp}[-[(Hm-T*S)/(1.987*T)]]} \quad \text{Equation 1}$$

where, Yu and Yf are fit and represent the Y-intercept of the pre- and post-transition baselines, respectively. Mu and Mf are fit and represent the slope of the pre- and post-transition baselines, respectively. Hm and S are fit and represent enthalpy and entropy, respectively. T is the measured temperature in Kelvin units.

In experiments conducted essentially as described above in this Example 7, the Tm values for human pro-BMP7 wild type and human pro-BMP7 protein variant V114M are 61° C. and 64.5° C., respectively, indicating that a variant of human pro-BMP7 of the present invention has an increased thermal unfolding stability, i.e., is more stable than wild type human pro-BMP7.

EXAMPLE 8

Ectopic Bone Formation Model

Ectopic bone formation (EBF) may be measured in female CB17SC-M SCID mice upon subcutaneous administration of certain human BMP7 protein variants of the present invention compared to wild type human mature BMP7.

Briefly described, the mice may be anesthetized with 3% isoflurane and are injected with 3 μg/100 μl of the human BMP7 protein variant, wild type human mature BMP7 protein or a vehicle control on the back left flank. The back right flank of each mouse may serve as a control (no injection). Vehicle (pH 4.5): 0.5% Sucrose, 2.5% Glycine, 5 mM L-Glutamic Acid, 5 mM NaCl, 0.01% polysorbate 80, and, 0.1% BSA.

EBF may be measured by a CT scan on Day 13 after injection of the human BMP7 protein variant or wild type human mature BMP7 protein.

The data obtained from experiments conducted essentially as described above in this Example 8 suggests that despite increased potency of certain human BMP7 protein variants of the present invention, they demonstrate less EBF capability (see Table 6).

distribution between the osteoarthritic (right) and contralateral control (left) limb may be utilized as an index of joint discomfort (measure of pain) in the osteoarthritic knee. Results may be presented as the difference in weight bearing between the contralateral control (left) and the osteoarthritic (right).

In experiments conducted essentially as described above in this Example 9, treatment with human mature BMP7 protein variant F9 (SEQ ID NO: 8) at a dose of 0.175 μg/knee shows a significant decrease in pain beginning at day 38 and persisting, with the exception of day 45, until day 66 post-MIA compared to vehicle-treated controls. On the other hand, wild type human mature BMP7 (SEQ ID NO: 2) at a dose of 1 μg only shows a significant decrease in pain beginning at day 58. The data indicates that human mature BMP7 protein variant F9 (SEQ ID NO: 8) is more potent in decreasing pain compared to wild type human mature BMP7 (SEQ ID NO: 2)(see Table 7).

TABLE 7

| Treatment | Day 17 | Day 24 | Day 31 | Day 38 | Day 45 | Day 52 | Day 58 | Day 66 |
|---|---|---|---|---|---|---|---|---|
| Vehicle | 23.28 ± 3.60$^a$ | 23.30 ± 2.01 | 23.15 ± 2.24 | 22.48 ± 0.81 | 22.19 ± 1.07 | 22.75 ± 0.49 | 21.72 ± 1.69 | 22.14 ± 1.83 |
| Wild type BMP7 1.0 μg | 27.52 ± 2.81 | 26.05 ± 2.81 | 23.46 ± 1.23 | 22.68 ± 0.61 | 20.95 ± 0.87 | 20.37 ± 0.71 | 17.66 ± 1.79$^b$ | 17.59 ± 2.68$^b$ |
| SEQ ID NO: 8 0.175 μg | 23.29 ± 1.31 | 24.32 ± 2.97 | 21.87 ± 2.14 | 20.82 ± 1.03$^b$ | 19.44 ± 0.80 | 19.35 ± 0.77 | $^b$17.42 ± 3.16$^b$ | 15.00 ± 1.84$^b$ |
| SEQ ID NO: 8 0.7 μg | 36.75 ± 6.45$^b$ | 29.78 ± 8.39 | 26.62 ± 6.07 | 23.63 ± 0.90 | 21.75 ± 4.34 | 20.51 ± 3.03 | 16.72 ± 0.79$^b$ | 13.06 ± 1.78$^b$ |

Values are mean ± SD n = 6 per group;
$^a$Difference in hind paw weight bearing (g)
$^b$P <0.008 vs vehicle using a repeated measures analysis and treatment comparison by time point

TABLE 6

| Group | Ectopic Bone Formation Volume (mm$^3$) |
|---|---|
| Wild type human mature BMP7 (SEQ ID NO: 2) | 78 |
| Human mature BMP7 variant (SEQ ID NO: 7) | 11 |
| Human mature BMP7 variant F9 (SEQ ID NO: 8) | 7 |

EXAMPLE 9

MIA Rat Model of Osteoarthritic Pain

The effect of human mature BMP7 protein variant F9 (SEQ ID NO: 8) may be evaluated in the monosodium iodoacetate (MIA)-induced rat model of OA pain (Bove, et. al., Osteoarthritis and Cartilage, 2003, 11: 821-830).

Briefly stated, male Lewis rats aged 7-8 weeks at the time of MIA injection may be used for this study. For induction of osteoarthritis, the rats may be anesthesized with isoflurane and given a single intra-articular injection of 0.3 mg/50 μl MIA through the infrapatellar ligament of the right knee. The left contralateral control knee may be injected with 50 μl sterile saline. The animals are treated with wild type human mature BMP7 protein at a dose of 1.0 μg/knee and human mature BMP7 protein variant F9 (SEQ ID NO: 8) at 0.175 μg and 0.7 μg/knee via intra-articular injections on day 9 and 14 post-MIA.

Pain measurements may be made by incapacitance testing on days 17, 24, 31, 38, 45, 52, 58, and 66 post-MIA injection using an incapacitance tester (Columbus Instruments International, Columbus, Ohio). Changes in hind paw weight

EXAMPLE 10

Meniscal Tear Rat Model of Cartilage Degeneration

The effect of human mature BMP7 protein variant (SEQ ID NO: 8) may be evaluated using an osteoarthritic (OA) pain in the meniscal tear (MT) induced rat model of cartilage degeneration. Male Lewis rats (approximately 25 weeks of age) may be used for such a study. Briefly described, rats may be anesthetized with 3% isoflurane prior to surgery. The right knee may be flexed and a transverse medial incision is made along the proximal antero-medial aspect of the tibia exposing the medial contralateral ligament. The contralateral ligament and the joint capsule may be incised simultaneously freeing the tibial attachments of the medial meniscus. Approximately 3 mm of the meniscus may be freed from its attachment to the margin of the tibial plateau and the meniscus may be transected to simulate a complete tear. The incision may be closed with surgical glue.

The animals may be treated with wild type human mature BMP7 at a dose of 350 ng/knee or human mature BMP7 protein variant F9 (SEQ ID NO: 8) at two doses of 49 ng or 245 ng/knee in 50 μl phosphate buffered saline (PBS), pH 7.4. The treatment may be initiated 3 weeks after MT surgery and continued for approximately 8 weeks. Animals may be administered weekly intra-articular injections of wild type human mature BMP7 or human mature BMP7 protein variant F9 (SEQ ID NO: 8) or vehicle at various doses for 5 weeks into the operated knee. Pain measurements may be made by incapacitance testing on days 18 (baseline), 25, 31, 42 and 53 post MT surgery using an incapacitance tester (Columbus Instruments International, Columbus, Ohio). Changes in hind paw weight distribution between the osteoarthritic (right) and contralateral control (left) limb may be utilized as an index of joint discomfort (measure of pain) in the osteoarthritic knee. Results may be presented as the difference in weight bearing between the contralateral control (left) and the osteoarthritic (right).

In experiments conducted essentially as described above in this Example 10, MT surgery in the right knee results in an increase in joint discomfort as defined by change in the hind paw weight distribution (measure of pain)(see Table 8). Human mature BMP7 protein variant F9 (SEQ ID NO: 8) at a dose of 245 ng/knee or a dose of 49 ng/knee showed a significant decrease in pain compared to vehicle-treated controls beginning at day 31 and persisting until day 53. Treatment with wild type human mature BMP7 at a dose of 350 ng/knee showed a decrease in pain at only 42 days post-MT surgery compared to vehicle treated controls. The data indicates that treatment with human mature BMP7 protein variant F9 (SEQ ID NO: 8) is more effective in decreasing pain compared to wild type human mature BMP7 in the rat MT-induced model of OA pain.

TABLE 8

|   | Baseline | Day 25 | Day 31 | Day 42 | Day 53 |
|---|---|---|---|---|---|
| A | $51.62 \pm 3.08^a$ | $51.35 \pm 1.34$ | $53.42 \pm 2.10$ | $52.5 \pm 1.34$ | $49.57 \pm 2.35$ |
| B | $52.33 \pm 2.45$ | $50.76 \pm 1.09$ | $49.97 \pm 1.10$ | $46.81 \pm 1.34^b$ | $47.77 \pm 1.78$ |
| C | $52.48 \pm 2.11$ | $49.96 \pm 0.66$ | $49.52 \pm 1.10^b$ | $44.8 \pm 3.04^b$ | $45.70 \pm 2.77$ |
| D | $52.02 \pm 2.19$ | $49.77 \pm 1.00$ | $49.54 \pm 2.77^b$ | $42.37 \pm 1.28^b$ | $38.68 \pm 1.68^b$ |

Treatment A: Vehicle
Treatment B: Wild type human mature BMP7 (SEQ ID NO: 2); 350 ng
Treatment C: Human mature BMP7 protein variant F9 (SEQ ID NO: 8); 49 ng
Treatment D: Human mature BMP7 protein variant F9 (SEQ ID NO: 8); 245 ng
Values are mean ± SD, n = 6 per group
$^a$Difference in hind paw weight bearing (g)
$^b$P < 0.05 vs vehicle using a repeated measures analysis and treatment comparison by time point

EXAMPLE 11

Proteoglycan Synthesis in Human Articular Osteoarthritic Chondrocytes

Proteoglycan synthesis in human articular osteoarthritic (OA) chondrocytes is an n vitro model for chondrocyte activity. The effect of human mature BMP7 protein variants may also be evaluated on proteoglycan synthesis m human articular OA chondrocytes in vitro and compared to wild type human mature pro-BMP7. The proteoglycan synthesis may be measured using $^{35}$S incorporation. Arthritic human knee cartilage is obtained from donors at surgery. The cartilage pieces may be finely chopped and chondrocytes may be isolated from the associated matrix by enzymatic digestions. The cartilage may be first digested with 1 mg/ml pronase in DMEM/PRF (phenol red free) media with 5% Fe supplemented calf serum (FCS) and 2% penicillin-streptomycin-antimycotic for 60 minutes followed by overnight digestion with 1 mg/ml collagenase II in DMEM/PRF media with 5% FCS) and 2% penicillin-streptomycin-antimycotic at 37° C. The cells may be washed with DMEM/F-12 media and then resuspended in DMEM/F-12 with 5% FCS and counted with a Coulter counter. The cells may be plated at a density of 30,000 cells/well in 96-well collagen coated CytoStar T plate in growth media containing DMEM, 5% FCS. ITS (insulin, transferin, selenium) and 1% penicillin-streptomycin-antimycotic. After 24 hours, the media may be replaced with 100 μl of growth media containing 10 μCi/ml (1 μCi/well) of $^{35}$S and treated with wild type human pro-BMP7 or a human pro-BMP7 protein variants at various doses. Then the cells may be incubated for approximately 7 days at 37° C. with 5% $CO_2$. At the end of the treatment period the media may be removed, replaced with phosphate buffered saline and $^{35}$S incorporation is counted using a Wallac 1450 MicroBeta TriLux Liquid Scintillation Counter & Luminometer.

In experiments conducted essentially as described above in this Example 11, cells treated with human pro-BMP7 protein variant (SEQ ID NO: 16) demonstrate a significant increase in proteoglycan synthesis at doses ranging between 1.2 to 300 ng/ml (see Table 9). In contrast, wild type human pro-BMP7 shows a significant increase only at the 300 ng/ml dose. Thus, human pro-BMP7 protein variant (SEQ ID NO: 16) is more potent in stimulating proteoglycan synthesis compared to wild type human pro-BMP7 in rat primary human OA articular chondrocytes.

TABLE 9

| | Proteoglycan Synthesis* (CPMs) | | |
|---|---|---|---|
| Treatment (ng) | Control | Human wild type pro-BMP7 | SEQ ID NO: 16 |
| 0 | $580 \pm 84$ | NT | NT |
| 0.1 | NT | $679 \pm 120$ | $654 \pm 93$ |
| 0.4 | NT | $724 \pm 120$ | $729 \pm 133$ |
| 1.2 | NT | $679 \pm 120$ | $1197 \pm 98^a$ |
| 3.7 | NT | $666 \pm 130$ | $1991 \pm 224^a$ |
| 11 | NT | $723 \pm 72$ | $3822 \pm 263^a$ |
| 33 | NT | $799 \pm 65$ | $4191 \pm 355^a$ |
| 100 | NT | $1500 \pm 309$ | $4235 \pm 202^a$ |
| 300 | NT | $3325 \pm 237^a$ | $4219 \pm 75^a$ |

Values are mean ± SD;
n = 3/group
*Proteoglycan synthesis measured by $^{35}$S incorporation
$^a$P < 0.05 vs untreated control
CPM—counts per minute
NT—Not tested

EXAMPLE 12

Chondrogenesis Assay

The effect of wild type human mature BMP7 and variants thereof may be evaluated for differentiation of chondrocytes in an in vitro model utilizing rat primary articular chondrocytes (RPACs). To obtain RPACs, articular cartilage may be isolated from 2-3 day old rats. The cartilage may be digested with 0.4% collagenase for 2 hours and then the resultant cells may be washed with phosphate buffered saline and subsequently cultured in media containing DMEM, 10% FBS and 1% penicillin/streptomycin in humidified air with 5% $CO_2$ at 37° C.

To assess the chondrogenic differentiation, a pellet culture system may be used. Approximately $2 \times 10^5$ cells from passage 2-3 may be placed in 1.5 ml tubes and centrifuged at 500 g for 10 minutes. The pellets may be cultured at 37° C. with 5% $CO_2$ in 500 µl of medium. The effect of wild type human mature BMP7 or human mature BMP7 protein variants may be tested at various concentrations, such as 0.02, 0.2 and/or 2 µM. The media may be replaced twice per week for 2 weeks. After 2 weeks in culture, the pellets may be harvested and macroscopic analysis was performed by stereomicroscopic procedures. The images may be analyzed and the pellet sizes may be calculated in a 2-dimensional image.

In experiments conducted essentially as described above in this Example 12, pellets treated with human mature BMP7 protein variant F9 (SEQ ID NO: 8) are significantly larger compared to those that were treated with wild type human mature BMP7 or untreated controls (see Table 10). The increases in pellet sizes are observed in a dose-dependent manner, but are most prominent at 0.14 and 1.4 nM concentrations. The data demonstrates that human mature BMP7 protein variant F9 (SEQ ID NO: 8) is more potent in increasing pellet sizes compared to wild type human mature BMP7 in rat primary articular chondrocytes (see Table 10). Because cell pellet sizes are indicative of increased cell proliferation, human mature BMP7 protein variant F9 (SEQ ID NO: 8) appears to be much more potent in increasing the proliferation of rat primary articular chondrocytes compared to wild type human mature BMP7.

TABLE 10

| Treatment (nM) | Control | Pellet Size (mm$^2$) WT human mature BMP7 | Human mature BMP7 protein variant F9 (SEQ ID NO: 8) |
| --- | --- | --- | --- |
| 0 | 0.51 ± 0.05 | NT | NT |
| 0.014 | NT | NT | 0.67 ± 0.16 |
| 0.14 | NT | NT | 1.56 ± 0.46$^a$ |
| 1.4 | NT | NT | 2.61 ± 0.18$^a$ |
| 0.02 | NT | 0.64 ± 0.15 | NT |
| 0.2 | NT | 0.70 ± 0.03 | NT |
| 2 | NT | 0.83 ± 0.13 | NT |

Values are mean ± SD;
n = 3/group
$^a$P < 0.05 vs untreated control
NT—Not tested

EXAMPLE 13

Bone Healing Model

The effect of wild type human mature BMP7 and variants thereof may be evaluated on bone regeneration and repair or bone healing in a rat surgical fracture model. Animals may be ovariectomized at 6 months of age and allowed to lose bone for two months before fracture surgery. Cortical defect surgery may be performed essentially as previously described (Komatsu, et al., Endocrinology, 150:1570-1579, 2009). Briefly, the procedure involves incising the skin over the lateral femoral aspect and blunt dissection of the quadriceps to expose the distal femoral diaphysis. Cortical defects may be then generated through the anterior and posterior cortexes using a Dremel tool (Robert Bosch Tool Corp, Gerlingen, Germany) equipped with a 2 mm orthopedic drill bit (Zimmer Inc, Warsaw, Ind.). The muscles may be subsequently repositioned, and the skin may be closed with tissue adhesive. Groups of animals may be treated with various amounts of wild type human mature BMP7 or variants thereof prepared in sodium citrate buffer pH 3.0 and adsorbed to Helistat type-1 collagen sponges in a volume of 50 µl. The treatments may be administered locally at the site of defect during surgery and treated for 35 days. A control group may receive the vehicle containing the same constituents in collagen sponge without the therapeutic proteins. In vivo fracture repair and bone mineral content (BMC) may be evaluated by quantitative computed tomography (QCT) using a GE Locus Ultra CT scanner (GE Healthcare, London, Ontario, Canada) as described previously (Komatsu et al., 2008).

In experiments conducted essentially as described above in this Example 13, treatment with 16.5 µg human mature BMP7 protein variant F9 (SEQ ID NO: 8) showed a significant increase in BMC and cortical area by forming new cortical shell on day 35 after treatment (see Table 11). On the other hand, treatment with 16.5 µg wild type human mature BMP7 did not show a significant change in BMC on day 35. The data demonstrates that human mature BMP7 protein variant F9 (SEQ ID NO: 8) is potent in increasing BMC and cortical area compared to wild type human mature BMP7 in a rat cortical defect bone healing model.

TABLE 11

| Treatment | BMC (mg) | % Increase From Vehicle Control |
| --- | --- | --- |
| A | 14.11 ± 1.50 | 100 |
| B | 16.25 ± 1.60 | 115 |
| C | 16.19 ± 1.09 | 114 |
| D | 18.13 ± 2.29$^a$ | 128 |

Treatment A: Vehicle
Treatment B: Wild type human mature BMP7 (SEQ ID NO: 2); 16.5 µg
Treatment C: Human mature BMP7 protein variant F9 (SEQ ID NO: 8); 2.0 µg
Treatment D: Human mature BMP7 protein variant F9 (SEQ ID NO: 8); 16.5 µg
Values are mean ± SEM; n = 6-8/group
$^a$P < 0.05 vs untreated vehicle

EXAMPLE 14

Established Cord Assay

An in vitro endothelial cord formation assay, a surrogate of angiogenesis, may be used to investigate the role of human BMP7 proteins on various growth factor established cords including, but not limited to, VEGF, basic FGF, and EGF established cords. Endothelial cord forming cells (ECFCs; passage 4-10 suitable for cord formation) may be cultured in EGM-2 MV (Lona) media containing a final concentration of 10% FBS and passaged onto type 1 collagen (fibrillar) coated flasks prior to seeding into the cord formation assay in vitro. Adipocyte derived stem cells (Zen-Bio, cells frozen at passage 4; cells at passage 5 or greater not assayed) may be cultured in EGM-2 MV (Lonza) media prior to plating at 50,000 cells per well (into 96-well black poly-D-lysine coated plates) in co-culture media [for example, MCDB-131 media (Invitrogen) supplemented with 30 µg/ml L-ascorbic acid 2-phosphate, 1 µM dexamethasone, 50 µg/ml tobramycin, 10 µg/ml insulin (all from Sigma-Aldrich), and 10 µg/ml cell prime r-transferrin AF (Millipore, Billerica, Mass.)] for 24 hours. Adipocyte derived stem cell (ADSC) media may be removed and 5,000 ECFCs (Lonza) per well may be over seeded. Approximately 4 hours following ECFC plating, the cords may be treated with 10 ng/ml VEGF, 10 ng/ml bFGF, or 10 ng/ml EGF (all from Biosource International) and exposure to growth factors may be continued for approximately 120 hours. Then, PBS controls, human BMP7 proteins including human BMP7 protein variants of the present invention (100 ng/ml), or sunitinib may be added and incubated for 96 hours. All cell culture incubations may be conducted at 37° C., 5% $CO_2$. Then the cells may be directly fixed for 10 minutes with 3.7% formaldehyde (Sigma Aldrich) followed by ice-cold 70% ethanol for 20 minutes at 25° C. Cells may be rinsed once with PBS, blocked for 30 minutes with 1% BSA and immuno-stained for 1 hour with antiserum directed against CD31 (R&D Systems. Minneapolis, Minn.) diluted to 1 µg/ml in 1% BSA. Then the cells may be washed 3 times with PBS and incubated for 1 hour with 5 µg/ml donkey α-sheep-Alexa-488 (Invitrogen), α-Smooth Muscle Actin Cy3 conjugate (1:200, Sigma-Aldrich), and 200 ng/ml Hoechst 33342 (Invitrogen) in 1% BSA. Afterwards, the cells may be washed with PBS, then imaged using the cord formation algorithms on the Cellomics ArrayScan VTI at an image magnification of 5× (Thermo Fisher Scientific, Pittsburgh, Pa.).

In experiments conducted essentially as described above in this Example 14, sunitinib (100 nM), an agent with an anti-angiogenic mechanism of action, was used as a positive control. Human pro-BMP7-F9 (100, 50, 25, and 12.5 ng/ml) was determined to reduce established cord connected tube area (% PBS control) of endothelial cords that were allowed to form for 120 hours in the presence of the indicated growth factors prior to compound treatment (growth factors remained for duration of experiment).

Human Pro-BMP7 Variant F9 Reduced VEGF-Driven Cord Formation

An ADSC/ECFC co-culture was unstimulated (basal) or stimulated with 10 ng/ml VEGF and treated simultaneously with PBS or 100 ng/ml human pro-BMP7 variant F9 or 100 nM sunitinib for 96 hours prior to immunohistochemistry for CD31 (green), α-smooth muscle actin (red), and Hoechst 33342 to stain all nuclei (blue). Resulting CD31-positive endothelial cords were visualized and quantitated using high content imaging. Results are shown in Table 12. Values represent % PBS controls, mean±SD; n=8/treatment group, n=16 in PBS control groups.

TABLE 12

|  | Connected Tube Area - VEGF (% PBS) |
| --- | --- |
| PBS | 100.0 ± 14.90% |
| BMP7F9 100 ng/ml | 18.66 ± 3.72% |
| 100 nM sunitinib | 26.14 ± 9.88% |

Human Pro-BMP7 Variant F9 Reduced FGF-Driven Cord Formation

An ADSC/ECFC co-culture was unstimulated (basal) or stimulated with 10 ng/ml bFGF and treated simultaneously with PBS or 100 ng/ml human pro-BMP7 variant F9 or 100 nM sunitinib for 96 hours prior to immunohistochemistry for CD31 (green), α-smooth muscle actin (red), and Hoechst 33342 to stain all nuclei (blue). Resulting CD31-positive endothelial cords were visualized and quantitated using high content imaging. Results are shown in Table 13. Values represent % PBS controls, mean±SD; n=8/treatment group, n=16 in PBS control groups.

TABLE 13

|  | Connected Tube Area - FGF (% PBS) |
| --- | --- |
| PBS | 100.0 ± 18.67% |
| BMP7F9 100 ng/ml | 4.39 ± 2.80% |
| 100 nM sunitinib | 43.01 ± 18.28% |

Human Pro-BMP7 Variant F9 Reduced EGF-Driven Cord Formation

An ADSC/ECFC co-culture was unstimulated (basal) or stimulated with 10 ng/ml EGF and treated simultaneously with PBS or 100 ng/ml human pro-BMP7 variant F9 or 100 nM sunitinib for 96 hours prior to immunohistochemistry for CD31 (green), α-smooth muscle actin (red), and Hoechst 33342 to stain all nuclei (blue). Resulting CD31-positive endothelial cords were visualized and quantitated using high content imaging. Results are shown in Table 14. Values represent % PBS controls, mean±SD; n=8/treatment group, n=16 in PBS control groups.

TABLE 14

|  | Connected Tube Area - EGF (% PBS) |
| --- | --- |
| PBS | 100.0 ± 22.16% |
| BMP7F9 100 ng/ml | 13.21 ± 2.59% |
| 100 nM sunitinib | 9.89 ± 8.059% |

These results indicate that human pro-BMP7 protein variant F9 reduces existing, established-growth factor induced endothelial cords in a surrogate in vitro angiogenesis assay.

EXAMPLE 15

BMP7 Protein Variant Inhibition of Tumor Growth in Mouse Xenograft Models for Colon Cancer Xenograft animal models may be used to assess the effectiveness of the human BMP7 protein variants of the present invention (as compared to the corresponding wild type human BMP7 protein) against specific types of cancer. More specifically, compounds may be tested on staged tumor growths that have been engrafted via subcutaneous or orthotopic inoculation in an immunocompromised mouse or rat model. Xenograft studies can be highly complex, starting with the selection of the appropriate animal model, choice of tumorigenic cell line, administration method, administration regimen, dosing, analysis of tumor growth rates and tumor analysis (histology, mRNA and protein expression levels).

The effect of various BMP7 protein variants on xenograft models of specific cancer were tested as described below.

Female athymic nude mice age 6- to 7-weeks old are available commercially, including from Harlan Laboratories (Indianapolis, Ind.). The mice are allowed to acclimate for one week and fed ad libitum on a normal low fat (4.5%) diet, which may be continued for the duration of the study. Tumor cells are available for purchase from ATCC and may be cultured in cell culture media such as RPMI 1640 (Life Technologies) with L-glutamine, 25 mM HEPES supplemented with 10% FBS and 1 mM Na Pyruvate. Cells may be detached, washed with serum free medium and then resuspended at a final concentration of 50×106 cells/mL in serum free RPMI 1640. Tumor cells, approximately 5×106 may be injected subcutaneously in the rear flank of subject mice in a 1:1 mixture of serum free growth medium and Matrigel (Becton Dickinson, Bedford, Mass.). Tumor and body weight measurements may be performed twice weekly. Prior to treatment, mice can be randomized based on tumor size using a randomization algorithm. Treatments may be started when the average tumor volume reaches 100 mm3. The randomized mice were separated into different groups and dosed with compounds through tail vein injection once a week.

All test or control proteins are prepared in phosphate Buffered Saline (PBS) prior to dose. Tumor size may be determined by caliper measurements. Tumor volume (mm3) may be estimated from the formula A2×B×0.536, where A is the smaller and B is the larger of perpendicular diameters. Tumor volume data can be transformed to a log scale to equalize variance across time and treatment groups. Log volume data can be analyzed with two-way repeated measures ANOVA by time and treatment using SAS PROC MIXED software (SAS Institutes Inc, Cary, N.C.). Treatment Groups are Compared with the Specified Control Group at Each Time Point.

Immunodeficient mice bearing DLD1 C5 tumor xenografts (Wnt/TCF-1 driven colon cancer model) may be generated as described above in this Example 15 and treated with either vehicle control, the human mature BMP7 variant F9, irinotecan, or the combination of the human mature BMP7 variant F9 and irinotecan, three times/week (BMP7 variant F9) or twice/week (irinotecan) for approximately 3-6 consecutive weeks.

In a DLD1 C5 mouse xenograft tumor model conducted essentially as described above in this Example 15, tumor regression was observed in a DLD1 C5 mouse xenograft model when they were pre-treated with human mature BMP7 variant F9 for three weeks followed by 3 weeks of therapy with irinotecan. Specifically, the administration of the human mature BMP7 variant F9 for 3 weeks followed by 3 weeks of therapy with irinotecan (dosed IP at 0.04 mg/kg MWF, and 20 mg/kg, M and Th, respectively) induced DLD1 C5 tumor sensitivity to the chemotherapeutic agent irinotecan (immediate tumor regression) relative to saline-treated, then irinotecan treated animals (which resulted in tumor growth).

EXAMPLE 16

Endogenous BMP7 Inhibitor Activity on BMP7 Protein Variants

Endogenous BMP antagonists such as noggin, Sost, follistatin, twisted gastrulation (TSG), chordin, and members of the gremlin, Cerberus and Dan families of proteins for example act on BMP family of proteins in vivo to modulate the BMP activities including those relating to growth, differentiation and activity of a range of cells. As with BMPs themselves, expression of the various antagonists is under tight spatiotemporal control. (see, Bone Morphogenic Proteins and Their Antagonists, Vitamins and Hormones (2015), volume 99, pages 63-90; Editor Gerald Litwack). The effect of various BMP antagonists on human BMP7 proteins and variants thereof may be tested in an in vitro assay as described below in this Example 16.

Briefly described, Hep3B2 cells stably transfected with a hepcidin promoter luciferase construct (hereinafter, referred to as Hep3B2_HepPro_luc cells) were used for BMP inhibitor experiments. Hep3B2_HepPro_luc cells may be plated at 30,000 cells per well in a tissue culture treated 96 well plate in DMEM (Hyclone) 5% FBS (Gibco) supplemented with non-essential amino acids (Hyclone) and 200 μg/ml gentecin (Hyclone) for 24 hours. Cells were then starved in OMEM+ 0.2% BSA for 5 hours. Cells were treated with a mixture of human BMP7 proteins and variants thereof in OMEM (Gibco)+0.2% BSA (Gibco) for 18 hours then developed for luciferase activity utilizing Luciferase reporter Gene Assay Kit (Roche). BMP7 proteins were added at concentrations in the linear range of the assay, at 1 nM and 100 pM. Inhibitors were added at various concentrations in molar excess of the particular BMP7 protein being tested. All BMP inhibitors except Follistatin were purchased from R&D Systems. Follistatin and BMP7 proteins and variants thereof were generated at Eli Lilly and Company.

In experiments conducted essentially as described above in this Example 16, wild type BMP7 proteins were significantly more susceptible to inhibition by certain BMP antagonists as compared to the corresponding (i.e., pro- or mature) form of the BMP7 F9 variant of the present invention (see Table 15).

TABLE 15

| | % inhibition | | | | |
| --- | --- | --- | --- | --- | --- |
| Molar excess of inhibitor | 100X | 10X | 1X | 0.1X | 0.01X BMP Inhibitor |
| BMP7-F9 Pro | 22.5* | 11.7 | −4.3 | −2.6 | Follistatin |
| BMP7 WT Pro | 79.8 | 29.5 | 5.9 | −10.4 | |
| BMP7-F9 mature | | 23.8 | 10.0 | 10.6 | 3.9 |
| BMP7 WT mature | 54.7 | 21.1 | −11.9 | −16.6 | |
| BMP7-F9 Pro | 24.9* | 8.8* | 2.4* | 3.5* | Chordin-like 2 |
| BMP7 WT Pro | 88.2 | 87.5 | 55.9 | 8.9 | |
| BMP7-F9 mature | | 9.0 | −1.0 | −3.2 | −1.5 |
| BMP7 WT mature | 71.9 | 69.5 | 49.0 | −13.7 | |
| BMP7-F9 Pro | −28.1* | −23.6* | −18.3 | −15.2 | Noggin |
| BMP7 WT Pro | 87.3 | 84.8 | 24.8 | −5.3 | |
| BMP7-F9 mature | | −1.2 | −6.9 | −7.2 | −2.6 |
| BMP7 WT mature | 73.7 | 72.8 | 36.7 | −12.2 | |
| BMP7-F9 Pro | −17.7* | −1.3 | −5.3 | −5.9 | Chordin |
| BMP7 WT Pro | 76.5 | 18.9 | −2.2 | −15.1 | |
| BMP7-F9 mature | | 5.6 | 5.2 | 6.8 | 3.7 |
| BMP7 WT mature | 70.9 | 21.3 | −9.2 | −13.1 | |
| BMP7-F9 Pro | 754# | 7.0 | −27.5 | −35.4 | Coco |
| BMP7 WT Pro | 81.6 | 17.4 | 4.0 | −10.2 | |
| BMP7-F9 mature | | 28.5 | 7.3 | 7.0 | 2.3 |
| BMP7 WT mature | 77.4 | 37.6 | −25.9 | −23.6 | |

*indicates inhibition of human BMP7 F9 variant form was significantly lower than inhibition the corresponding wild type form of human BMP7 protein
indicates human BMP7 F9 variant form and human WT form were inhibited about equally.

LISTING OF VARIOUS SEQUENCES

SEQ ID NO: 1
MHVRSLRAAAPHSFVALWAPLFLLRSALADFSLDNEVHSSFIHRRLRSQERREMQ
REILSILGLPHRPRPHLQGKHNSAPMFMLDLYNAMAVEEGGGPGGQGFSYPYKA
VFSTQGPPLASLQDSHFLTDADMVMSFVNLVEHDKEFFHPRYFIHREFRFDLSKIP
EGEAVTAAEFRIYKDYIRERFDNETFRISVYQVLQEHLGRESDLFLLDSRTLWASE
EGWLVFDITATSNHWVVNPRHNLGLQLSVETLDGQSINPKLAGLIGRHGPQNKQ
PFMVAFFKATEVHFRSIRSTGSKQRSQNRSKTPKNQEALRMANVAENSSSDQRQ
ACKKHELYVSFRDLGWQDWIIAPEGYAAYYCEGECAFPLNSYMNATNHAIVQTL
VHFINPETVPKPCCAPTQLNAISVLYFDDSSNVILKKYRNMVVRACGCH

SEQ ID NO: 2
STGSKQRSQNRSKTPKNQEALRMANVAENSSSDQRQACKKHELYVSFRDLGWQ
DWIIAPEGYAAYYCEGECAFPLNSYMNATNHAIVQTLVHFINPETVPKPCCAPTQ
LNAISVLYFDDSSNVILKKYRNMVVRACGCH

SEQ ID NO: 3
STGSKQRSQNRSKTPKNQEALRMANVAENSSSXaa$_{33}$QRQXaa$_{37}$CKKHELYVSFRD
LGWQDWIIAPXaa$_{60}$GYAAXaa$_{65}$YCEGECAFPLNSYMNATNHAXaa$_{86}$Xaa$_{87}$QXaa$_{89}$
LXaa$_{91}$HXaa$_{93}$Xaa$_{94}$NPETVPKPCCAPTQLXaa$_{110}$AISXaa$_{114}$LYFDDXaa$_{120}$SNVILKK
Xaa$_{128}$RNMXaa$_{132}$VXaa$_{134}$ACGCH

Wild type pro-domain + variant mature BMP7 (402 aa)
F93V/N110G
SEQ ID NO: 12
DFSLDNEVHSSFIHRRLRSQERREMQREILSILGLPHRPRPHLQGKHNSAPMFMLD
LYNAMAVEEGGGPGGQGFSYPYKAVFSTQGPPLASLQDSHFLTDADMVMSFVN
LVEHDKEFFHPRYHHREFRFDLSKIPEGEAVTAAEFRIYKDYIRERFDNETFRIS
VYQVLQEHLGRESDLFLLDSRTLWASEEGWLVFDITATSNHWVVNPRHNLGLQLSV
ETLDGQSINPKLAGLIGRHGPQNKQPFMVAFFKATEVHFRSIRSTGSKQRSQNRSK
TPKNQEALRMANVAENSSSDQRQACKKHELYVSFRDLGWQDWIIAPEGYAAYY
CEGECAFPLNSYMNATNHAIVQTLVHVINPETVPKPCCAPTQLGAISVLYFDDSS
NVILKKYRNMVVRACGCH Wild type pro-domain + variant mature BMP7 (402 aa)
Y65G/I86L/T89A/N110G
SEQ ID NO: 13
DFSLDNEVHSSFIHRRLRSQERREMQREILSILGLPHRPRPHLQGKHNSAPMFMLD
LYNAMAVEEGGGPGGQGFSYPYKAVFSTQGPPLASLQDSHFLTDADMVMSFVN
LVEHDKEFFEIPRYHHREFRFDLSKIPEGEAVTAAEFRIYKDYIRERFDNETFRIS
VYQVLQEHLGRESDLFLLDSRTLWASEEGWLVFDITATSNHWVVNPRHNLGLQLSV
ETLDGQSINPKLAGLIGRHGPQNKQPFMVAFFKATEVHFRSIRSTGSKQRSQNRSK
TPKNQEALRMANVAENSSSDQRQACKKHELYVSFRDLGWQDWIIAPEGYAAGY
CEGECAFPLNSYMNATNHALVQALVHFINPETVPKPCCAPTQLGAISVLYFDDSS
NVILKKYRNMVVRACGCH Wild type pro-domain + variant mature BMP7 (402 aa)
Y65G/I86L/Y128F/N110G
SEQ ID NO: 14
DFSLDNEVHSSFIHRRLRSQERREMQREILSILGLPHRPRPHLQGKHNSAPMFMLD
LYNAMAVEEGGGPGGQGFSYPYKAVFSTQGPPLASLQDSHFLTDADMVMSFVN
LVEHDKEFFEIPRYHHREFRFDLSKIPEGEAVTAAEFRIYKDYIRERFDNETFRIS -continued

VYQVLQEHLGRESDLFLLDSRTLWASEEGWLVFDITATSNHWVVNPRHNLGLQLSV

ETLDGQSINPKLAGLIGRHGPQNKQPFMVAFFKATEVHFRSIRSTGSKQRSQNRSK

TPKNQEALRMANVAENSSSDQRQACKKHELYVSFRDLGWQDWIIAPEGYAAGY

CEGECAFPLNSYMNATNHALVQTLVHFINPETVPKPCCAPTQLGAISVLYFDDSS

NVILKKFRNMVVRACGCH

Wild type pro-domain + variant mature BMP7 (402 aa)
Y65G/I86L/Y128W/N110G
SEQ ID NO: 15
DFSLDNEVHSSFIHRRLRSQERREMQREILSILGLPHRPRPHLQGKHNSAPMFMLD

LYNAMAVEEGGGPGGQGFSYPYKAVFSTQGPPLASLQDSHFLTDADMVMSFVN

LVEHDKEFFEIPRYHHREFRFDLSKIPEGEAVTAAEFRIYKDYIRERFDNETFRIS

VYQVLQEHLGRESDLFLLDSRTLWASEEGWLVFDITATSNHWVVNPRHNLGLQLSV

ETLDGQSINPKLAGLIGRHGPQNKQPFMVAFFKATEVHFRSIRSTGSKQRSQNRSK

TPKNQEALRMANVAENSSSDQRQACKKHELYVSFRDLGWQDWIIAPEGYAAGY

CEGECAFPLNSYMNATNHALVQTLVHFINPETVPKPCCAPTQLGAISVLYFDDSS

NVILKKWRNMVVRACGCH

Wild type pro-domain + variant mature BMP7 (402 aa)
Y65G/I86L/F93W/N110G/Y128W
SEQ ID NO: 16
DFSLDNEVHSSFIHRRLRSQERREMQREILSILGLPHRPRPHLQGKHNSAPMFMLD

LYNAMAVEEGGGPGGQGFSYPYKAVFSTQGPPLASLQDSHFLTDADMVMSFVN

LVEHDKEFFEIPRYHHREFRFDLSKIPEGEAVTAAEFRIYKDYIRERFDNETFRIS

VYQVLQEHLGRESDLFLLDSRTLWASEEGWLVFDITATSNHWVVNPRHNLGLQLSV

ETLDGQSINPKLAGLIGRHGPQNKQPFMVAFFKATEVHFRSIRSTGSKQRSQNRSK

TPKNQEALRMANVAENSSSDQRQACKKHELYVSFRDLGWQDWIIAPEGYAAGY

CEGECAFPLNSYMNATNHALVQTLVHVINPETVPKPCCAPTQLGAISVLYFDDSS

NVILKKWRNMVVRACGCH

SEQ ID NO: 17
STGSKQRSQNRSKTPKNQEALRMANVAENSSSXaa$_{33}$QRQXaa$_{37}$CKKHELYVSFRD

LGWQDWIIAPXaa$_{60}$GYAAXaa$_{65}$YCEGECAFPLNSYMNATNHAXaa$_{86}$VQXaa$_{89}$L

Xaa$_{91}$HXaa$_{93}$Xaa$_{94}$NPETVPKPCCAPTQLXaa$_{110}$AISXaa$_{114}$LYFDDSSNVILKK

Xaa$_{128}$RNMVVRACGCH
wherein at least one amino acid substitution that is:
Xaa$_{33}$ is D or M; Xaa$_{37}$ is A or P; Xaa$_{60}$ is E or Q; Xaa$_{65}$ is
Y, S, or G; Xaa$_{86}$ is I, V, or L; Xaa$_{89}$ is T, S, or A;
Xaa$_{91}$ is V or M; Xaa$_{93}$ is F or V; Xaa$_{94}$ is I, F or M; Xaa$_{110}$
is N, A, S, or G; Xaa$_{114}$ is V or M; and, Xaa$_{128}$ is Y, F or W.

SEQ ID NO: 18
DFSLDNEVHSSFIHRRLRSQERREMQREILSILGLPHRPRPFILQGKHNSAPMFMLD

LYNAMAVEEGGGPGGQGFSYPYKAVFSTQGPPLASLQDSHFLTDADMVMSFVN

LVEHDKEFFHPRYFIHREFRFDLSKIPEGEAVTAAEFRIYKDYIRERFDNETFRIS

VYQVLQEHLGRESDLFLLDSRTLWASEEGWLVFDITATSNHWVVNPRHNLGLQLSV

ETLDGQSINPKLAGLIGRHGPQNKQPFMVAFFKATEVHFRSIR (DNA SEQUENCE CORRESPONDING TO SEQ ID NO: 7)
SEQ ID NO: 19
ATGCACGTGCGCAGCCTGCGCGCCGCCGCCCCCCACAGCTT

CGTGGCCCTGTGGGCCCCCCTGTTCCTGCTGCGCAGCGCCCTGGCCGACT

TCAGCCTGGACAACGAGGTGCACAGCAGCTTCATCCACCGCCGCCTGCGC

-continued

```
AGCCAGGAGCGCCGCGAGATGCAGCGCGAGATCCTGAGCATCCTGGGCCT
GCCCCACCGCCCCCGCCCCCACCTGCAGGGCAAGCACAACAGCGCCCCCA
TGTTCATGCTGGACCTGTACAACGCCATGGCCGTGGAGGAGGCGGCGGC
CCCGGCGGCCAGGGCTTCAGCTACCCCTACAAGGCCGTGTTCAGCACCCA
GGGCCCCCCCCTGGCCAGCCTGCAGGACAGCCACTTCCTGACCGACGCCG
ACATGGTGATGAGCTTCGTGAACCTGGTGGAGCACGACAAGGAGTTCTTC
CACCCCCGCTACCACCACCGCGAGTTCCGCTTCGACCTGAGCAAGATCCC
CGAGGGCGAGGCCGTGACCGCCGCCGAGTTCCGCATCTACAAGGACTACA
TCCGCGAGCGCTTCGACAACGAGACCTTCCGCATCAGCGTGTACCAGGTG
CTGCAGGAGCACCTGGGCCGCGAGAGCGACCTGTTCCTGCTGGACAGCCG
CACCCTGTGGGCCAGCGAGGAGGGCTGGCTGGTGTTCGACATCACCGCCA
CCAGCAACCACTGGGTGGTGAACCCCGCCACAACCTGGGCCTGCAGCTG
AGCGTGGAGACCCTGGACGGCCAGAGCATCAACCCCAAGCTGGCCGGCCT
GATCGGCCGCCACGGCCCCCAGAACAAGCAGCCCTTCATGGTGGCCTTCT
TCAAGGCCACCGAGGTGCACTTCCGCAGCATCCGCAGCACCGGCAGCAAG
CAGCGCAGCCAGAACCGCAGCAAGACCCCCAAGAACCAGGAGGCCCTGCG
CATGGCCAACGTGGCCGAGAACAGCAGCAGCGACCAGCGCCAGGCCTGCA
AGAAGCACGAGCTGTACGTGAGCTTCCGCGACCTGGGCTGGCAGGACTGG
ATCATCGCCCCTGAGGGCTACGCCGCCGGCTACTGCGAGGGCGAGTGCGC
CTTCCCCCTGAACAGCTACATGAACGCCACCAACCACGCCCTGGTGCAGA
CCCTGGTGCACTTCATCAACCCCGAGACCGTGCCCAAGCCCTGCTGCGCC
CCCACCCAGCTGGGCGCCATCAGCGTGCTGTACTTCGACGACAGCAGCAA
CGTGATCCTGAAGAAGTGGCGCAACATGGTGGTGCGCGCCTGCGGCTGCC AC
```

(DNA SEQUENCE CORRESPONDING TO SEQ ID NO: 8)

SEQ ID NO: 20

```
ATGCACGTGCGCAGCCTGCGCGCCGCCGCCCCCCACAGCTTCGTGGCCCT
GTGGGCCCCCCTGTTCCTGCTGCGCAGCGCCCTGGCCGACTTCAGCCTGG
ACAACGAGGTGCACAGCAGCTTCATCCACCGCCGCCTGCGCAGCCAGGAG
CGCCGCGAGATGCAGCGCGAGATCCTGAGCATCCTGGGCCTGCCCCACCG
CCCCCGCCCCCACCTGCAGGGCAAGCACAACAGCGCCCCCATGTTCATGC
TGGACCTGTACAACGCCATGGCCGTGGAGGAGGGCGGCGGCCCCGGCGGC
CAGGGCTTCAGCTACCCCTACAAGGCCGTGTTCAGCACCCAGGGCCCCCC
CCTGGCCAGCCTGCAGGACAGCCACTTCCTGACCGACGCCGACATGGTGA
TGAGCTTCGTGAACCTGGTGGAGCACGACAAGGAGTTCTTCCACCCCCGC
TACCACCACCGCGAGTTCCGCTTCGACCTGAGCAAGATCCCCGAGGGCGA
GGCCGTGACCGCCGCCGAGTTCCGCATCTACAAGGACTACATCCGCGAGC
GCTTCGACAACGAGACCTTCCGCATCAGCGTGTACCAGGTGCTGCAGGAG
CACCTGGGCCGCGAGAGCGACCTGTTCCTGCTGGACAGCCGCACCCTGTG
GGCCAGCGAGGAGGGCTGGCTGGTGTTCGACATCACCGCCACCAGCAACC
ACTGGGTGGTGAACCCCGCCACAACCTGGGCCTGCAGCTGAGCGTGGAG
ACCCTGGACGGCCAGAGCATCAACCCCAAGCTGGCCGGCCTGATCGGCCG
CCACGGCCCCCAGAACAAGCAGCCCTTCATGGTGGCCTTCTTCAAGGCCA
```

-continued

```
CCGAGGTGCACTTCCGCAGCATCCGCAGCACCGGCAGCAAGCAGCGCAGC

CAGAACCGCAGCAAGACCCCCAAGAACCAGGAGGCCCTGCGCATGGCCAA

CGTGGCCGAGAACAGCAGCAGCGACCAGCGCCAGGCCTGCAAGAAGCACG

AGCTGTACGTGAGCTTCCGCGACCTGGGCTGGCAGGACTGGATCATCGCC

CCTGAGGGCTACGCCGCCGGCTACTGCGAGGGCGAGTGCGCCTTCCCCCT

GAACAGCTACATGAACGCCACCAACCACGCCCTGGTGCAGACCCTGGTGC

ACGTGATCAACCCCGAGACCGTGCCCAAGCCCTGCTGCGCCCCCACCCAG

CTGGGCGCCATCAGCGTGCTGTACTTCGACGACAGCAGCAACGTGATCCT

GAAGAAGTGGCGCAACATGGTGGTGCGCGCCTGCGGCTGCCAC
```

---

We claim:

1. A protein comprising a polypeptide comprising the amino acid sequence of:

(SEQ ID NO: 3)
STGSKQRSQNRSKTPKNQEALRMANVAENSSSXaa$_{33}$QRQXaa$_{37}$CK

KHELYVSFRDLGWQDWIIAPXaa$_{60}$GYAAXaa$_{65}$YCEGECAFPLNSY

MNATNHAXaa$_{86}$Xaa$_{87}$QXaa$_{89}$LXaa$_{91}$HXaa$_{93}$Xaa$_{94}$NPETVP

KPCCAPTQLXaa$_{110}$AISXaa$_{114}$LYFDDXaa$_{120}$SNVILKKXaa$_{128}$

RNMXaa$_{132}$VXaa$_{134}$ACGCH, wherein:
Xaa$_{33}$ is D or M; Xaa$_{37}$ is A or P; Xaa$_{60}$ is E or Q; Xaa$_{65}$ is Y, S, or G; Xaa$_{86}$ is I, V, or L; Xaa$_{87}$ is V or L; Xaa$_{89}$ is T, S, or A; Xaa$_{91}$ is V or M; Xaa$_{93}$ is F or V; Xaa$_{94}$ is I, F, or M; Xaa$_{110}$ is G; Xaa$_{114}$ is V or M; Xaa$_{120}$ is S or Q; Xaa$_{128}$ is Y, F, or W; Xaa$_{132}$ is V, Q, or S; and Xaa$_{134}$ is R or K.

2. The protein of claim 1, wherein Xaa$_{33}$ is D; Xaa$_{37}$ is A; Xaa$_{60}$ is E; Xaa$_{87}$ is V; Xaa$_{89}$ is T or A; Xaa$_{91}$ is V; Xaa$_{94}$ is I; Xaa$_{120}$ is S; Xaa$_{132}$ is V; and Xaa$_{134}$ is R.

3. The protein of claim 2, wherein Xaa$_{65}$ is Y or G; and Xaa$_{86}$ is I or L.

4. The protein of claim 3, wherein Xaa$_{65}$ is G; Xaa$_{86}$ is L; Xaa$_{89}$ is T; Xaa$_{93}$ is V; and Xaa$_{128}$ is F or W.

5. The protein of claim 4, wherein Xaa$_{114}$ is V.

6. The protein of claim 5, wherein the amino acid sequence of the polypeptide is SEQ ID NO: 8.

7. The protein of claim 1, wherein the amino acid sequence of the polypeptide is selected from the group consisting of SEQ ID NO: 4, SEQ ID NO: 5, SEQ ID NO: 6, SEQ ID NO: 7, SEQ ID NO: 9, and SEQ ID NO: 10.

8. The protein of claim 1, wherein the N-terminus of the polypeptide is covalently fused to the C-terminus of a human BMP7 pro-domain polypeptide comprising an amino acid sequence of SEQ ID NO: 18.

9. The protein of claim 1, wherein the amino acid sequence of the polypeptide is selected from the group consisting of SEQ ID NO: 12, SEQ ID NO: 13, SEQ ID NO: 14, SEQ ID NO: 15, and SEQ ID NO: 16.

10. A pharmaceutical composition comprising a protein of claim 1, and one or more pharmaceutically acceptable excipients, diluents, or carriers.

11. The pharmaceutical composition of claim 10, wherein the protein is a disulfide linked homodimer.

12. The pharmaceutical composition of claim 11, wherein the composition further comprises a polypeptide having the amino acid sequence of SEQ ID NO: 18.

13. A method of treatment for cartilage damage and degeneration, pain associated with osteoarthritis, or bone healing comprising administering to a human patient in need thereof an effective amount of the protein of claim 1.

14. A method of treatment for cartilage damage and degeneration, pain associated with osteoarthritis, or bone healing comprising administering to a human patient in need thereof an effective amount of the pharmaceutical composition of claim 10.

15. A method of treatment for glioblastoma comprising administering to a human patient in need thereof an effective amount of the protein of claim 1 and an effective amount of all-trans retinoic acid (ATRA).

16. A method of treatment for glioblastoma comprising administering to a human patient in need thereof an effective amount of the pharmaceutical composition of claim 10 and an effective amount of all-trans retinoic acid (ATRA).

* * * * *